US006146847A

United States Patent [19]

Goffe et al.

[11] Patent Number: 6,146,847

[45] Date of Patent: Nov. 14, 2000

[54] STABILIZED TRANSIENT GENE EXPRESSION

[75] Inventors: Randal A. Goffe; Adeelia S. Goffe, both of Arlington, Wash.

[73] Assignee: Genespan Corporation, Bothell, Wash.

[21] Appl. No.: 09/093,449

[22] Filed: Jun. 8, 1998

Related U.S. Application Data

[63] Continuation-in-part of application No. PCT/US97/19860, Oct. 31, 1997, which is a continuation-in-part of application No. 08/833,747, Apr. 11, 1997, abandoned.

[60] Provisional application No. 60/030,109, Nov. 1, 1996.

[51] Int. Cl.[7] .......................... C12N 15/87; C12N 15/88; C12N 15/86

[52] U.S. Cl. ........................ 435/69.1; 435/455; 435/456; 435/458

[58] Field of Search .................................... 435/375, 455, 435/465, 69.1; 514/44

[56] References Cited

U.S. PATENT DOCUMENTS

| | | |
|---|---|---|
| 4,418,691 | 12/1983 | Yannas et al. . |
| 4,458,678 | 7/1984 | Yannas et al. . |
| 4,640,912 | 2/1987 | Hausman . |
| 4,711,780 | 12/1987 | Fahim . |
| 4,945,086 | 7/1990 | Benitz et al. . |
| 5,284,931 | 2/1994 | Springer et al. . |
| 5,523,286 | 6/1996 | McGlave et al. . |
| 5,534,261 | 7/1996 | Rodgers et al. . |
| 5,545,722 | 8/1996 | Naka . |
| 5,573,934 | 11/1996 | Hubbell et al. . |
| 5,593,814 | 1/1997 | Matsuda et al. . |
| 5,661,025 | 8/1997 | Szoka, Jr. et al. . |

FOREIGN PATENT DOCUMENTS

| | | |
|---|---|---|
| 0 486 917A2 | 11/1990 | European Pat. Off. . |
| 94/16737 | 8/1994 | WIPO . |
| 95/26718 | 10/1995 | WIPO . |

OTHER PUBLICATIONS

Crystal. Transfer of Genes to Humans: Early Lessons and Obstacles to Success. Science 270: 404–410, Oct. 1995.

Report and Recommendtations of the Panel to Assess the NIH Investment in Research on Gene Therapy, Orkin and Motulsky, co–chairs. The National Institutes of Health, Dec. 1995.

Goffe, A., and R. Goffe, "Chemical stabilizing agents for transient DNA in cell culture," 163rd *AAAS Nat'l Mtg. Sci. Innov. Expos.*, Poster No. A106, Seattle, WA, 1997.

Nordenberg, J., et al., "Inhibition of growth of human melanoma cells and enhancement of alkaline phosphatase activity by butyric acid," *Harefuah*, 111:59, 1986.

Goldstein, S., et al., "Enhanced transfection efficiency and improved cell survival after electroporation of G2/M–synchronized cells and treatment with sodium butyrate," *Nucleic Acids Research*, 17:3959–3972, 1989.

Gorman, C., and B. Howard, "Expression of recombinant plasmids in mammalian cells is enhanced by sodium butyrate," *Nucleic Acids Research*, 11:7631–7648, 1983.

Satoh, K. et al., "Effect of drugs on gene expression in mammalian cells: a highly efficient procedure to test large numbers of samples," *Nucleic Acids Research*, 21:4429–4430, 1993.

Beis, I., and A. Theophilidis, "Phosphofructokinase in the plerocercoids of *Shistocephalus solidus* (Cestoda: Pseudophyllidea)," *Int. J. Paristol.*, 12:389–394, 1982.

Morand, C., et al., "Importance of the modulation of glycolysis in the control of lactate metabolism by fatty acids in isolated heptocytes from fed rats," *Arch. Biochem. Biophys.*, 309:254–260, 1994.

Anderson, J. and S. Bridges, "Short–chain fatty acid fermentation products of plant fiber affect glucose metabolism of isolated rat hepatocytes," *Proc. Soc. Exptl. Biol. Med.*, 17:372–376, 1984.

Kormis, K.K. et al., "Prospects of Therapy of Liver Diseases with Foreign Genes," *Seminars in Liver Disease* 15:257–267 (1995).

Gorman, C., "High Efficiency Gene Transfer into Mammalian Cells," *DNA Cloning II, A Practical Approach*, (Glover, D.M., Ed) IRL Press, Oxford pp. 143–190 (1985).

Wynshaw–Boris, A. et al., "The Determination of Sequence Requirements for Hormonal Regulation of Gene Expression," *BioTechniques* 4:104–117 (1986).

"Guide to Eukaryotic Transfections with Cationic Lipid Reagents," (Life Technologies (Gibco BRL)).

Chen, C. and Okayama, H., "High–Efficiency Transformation of Mammalian Cells by Plasmid DNA," *Mol. Cell. Biol.* 7:2745–2752 (1987).

Alam, J. and Cook, J.L., "Reporter Genes: Application to the Study of Mammalian Gene Transcription," *Anal. Biochem.* 188:245–254 (1990).

Gorman, C.M. and Howard, B.H., "Expression of recombinant plasmids in mammalian cells is enhanced by sodium butyrate," *Nucleic Acids Research* 11:7631–7648 (1983).

Wolff, J.A. et al., "Direct Gene Transfer into Mouse Muscle in Vivo," *Science* 247:1465–1468 (1990).

Cohen, J., "Naked DNA Points Way to Vaccines," *Science* 259:1691–1692 (1993).

Wu, G.Y. and Wu, C.H., "Receptor–mediated Gene Delivery and Expression in Vivo," *J. Biol. Chem.* 263:14621–14624 (1988).

Chow, D.D. et al., "Targeting Small Unilamellar Liposomes to Hepatic Parenchymal Cells by Dose Effect," *J. Pharmacol. Exptl. Ther.* 248:506–513 (1989).

(List continued on next page.)

*Primary Examiner*—George C. Elliott
*Assistant Examiner*—Thomas G. Larson
*Attorney, Agent, or Firm*—Christensen O'Connor Johnson Kindness PLLC

[57] ABSTRACT

This invention provides methods and chemical agents for enhancing transient expression in eukaryotic cells. Also provided are a model system for achieving prolonged transient expression in solid tumors, a means for culturing hepatocytes without feeder cells or an extracellular matrix bonded to the substratum, a method for manipulating cellular metabolism to reduce the consumption of glucose and a means for inducing the secretion of an endogenous phosphatase activity.

37 Claims, 5 Drawing Sheets

OTHER PUBLICATIONS

Wu, C.H. et al., "Targeting Genes: Delivery and Persistent Expression of a Foreign Gene Driven by Mammalian Regulatory Elements in Vivo," *J. Biol. Chem.* 264:16985–16987 (1989).

Kaneda, Y. et al., "Introduction and Expression of the Human Insulin Gene in Adult Rat Liver," *J. Biol. Chem.* 264:12126–12129 (1989a).

Kaneda, Y. et al., "Increased Expression of DNA Cointroduced with Nuclear Protein in Adult Rat Liver," *Science* 243:375–378 (1989b).

Wilson, J.M. et al., "Hepatocyte–directed Gene Transfer in Vivo Leads to Transient Improvement of Hypercholesterolemia in Low Density Lipoprotein Receptor–deficient Rabbits," *J. Biol. Chem.* 267:963–967 (1992).

Wilson, J.M. et al., "A Novel Mechanism for Achieving Transgene Persistence in Vivo after Somatic Gene Transfer into Hepatocytes," *J. Biol. Chem.* 267:11483–11489 (1992b).

Chowdhury, N.R. et al., "Fate of DNA Targeted to the Liver by Asialoglycoprotein Receptor–mediated Endocytosis in Vivo," *J. Biol. Chem.* 268:11265–11271 (1993).

Perales, J.C. et al., "Gene transfer in vivo: Sustained expression and regulation of genes introduced into the liver by receptor–targeted uptake," *Proc. Natl. Acad. Sci. USA* 91:4086–4090 (1994).

Palermo, D.P. et al., "Production of analytical quantities of recombinant proteins in Chinese hamster ovary cells using sodium butyrate to elevate gene expression," *J. Biotechnol.* 19:35–48 (1991).

Boffa, L.C. et al., "Manifold Effects of Sodium Butyrate on Nuclear Function," *J. Biol. Chem.* 256:9612–9621 (1981).

Kruh, J., "Effects of sodium butyrate, a new pharmacological agent, on cells in culture," *Mol. Cell. Biochem.* 42:65–82 (1982).

Chabanas, A. et al., "Effects of Butyric Acid on Cell Cycle Regulation and Induction of Histone H1° in Mouse Cells and Tissue Culture," *J. Mol. Biol.* 183:141–151 (1985).

Parker, M.I. et al., "DNA Hypermethylation in Sodium Butyrate–treated WI–38 Fibroblasts," *J. Biol. Chem.* 261:2786–2790 (1986).

Kooistra, T. et al., "Butyrate stimulates tissue–type plasminogen–activator synthesis in cultured human endothelial cells," *Biochem. J.* 247:605–612 (1987).

Kaneko, Y. et al., "Alteration of Differentiation State of Human Hepatocytes Cultured with Novobiocin and Butyrate," *Canc. Res.* 50:3101–3105 (1990).

Nathan, D.F. et al., "Increased Cell Surface EGF Receptor Expression during the Butyrate–Induced Differentiation of Human HCT–116 Colon Tumor Cell Clones," *Exptl. Cell Res.* 190:76–84 (1990).

Kosaka, M. et al., "Reversible Effects of Sodium Butyrate on the Differentiation of F9 Embryonal Carcinoma Cells," *Exptl. Cell Res.* 192:46–51 (1991).

Oh, S.K.W. et al., "Substantial Overproduction of Antibodies by Applying Osmotic Presure and Sodium Butyrate," *Biotech. Bioeng.* 42:601–610 (1993).

Sidhu, J.S. and Omiecinski, C.J., "Modulation of xenobiotic–inducible cytochrome P450 gene expression by dexamethasone in primary rat hepatocytes," *Pharmacogenitics* 5:24–36 (1995).

Morrow, J.S. et al., "Butyrate Regulates Glycosylation of the Glycoprotein Hormone Alpha Subunit Secreted by 'Glucose–Starved' Human Liver Cells," *Biochemical and Biophysical Research Communications* 112:115–125 (1983).

Barsoum, J., "Stable Integration of Vectors at High Copy Number for High–Level Expression in Animal Cells," *Methods in Molecular Biology: Animal Cell Electroporation and Electrofusion Protocols* 48:225–237 (1995).

Berthold, W., "Gene Stability in Mammalian Cells and Protein Consistency," *Genetic Stability and Recombinant Product Consistency* 83:67–79 (1994).

Bilbao, G. et al., "Adenoviral/retroviral vector chimeras: a novel strategy to achieve high–efficiency stable transduction in vivo," *The FASEB Journal* 11:624–634 (1997).

BioWhitaker, Inc., "Multi–Test Limulus Amebocyte Lysate Pyrogent® 03 plus," pp. 1–11 (1995).

Boulo, V. et al., "Transient expression of luciferase reporter gene after lipofection in oyster (*Crassostrea gigas*) primary cell cultures," *Molecular Marine Biology and Biotechnology* 5(3):167–174 (1996).

Bray, H.G. et al., "Chondroitin from Cartilage," *Chemistry of Tissues* pp. 142–146 (1944).

Flamant, F. et al., "Virofection: a new procedure to achieve stable expression of genes transferred into early embryos," *Int. J. Dev. Biol.* 38:751–757 (1994).

Hascall, V.C., "Isolation and Characterization of Proteoglycans," *Methods in Enzymology* 230:390–417 (1994).

Kelleher, Z.T. and Vos, J.–M.H., "Long–Term Episomal Gene Delivery in Human Lymphoid Cells Using Human and Avian Adenoviral–Assisted Transfection," *BioTechniques* 17(6):1110–1117 (1994).

GibcoBRL Life Technologies, "1993–1994 Catalogue and Reference Guide," pp. R12–R19 (1993).

Matthews, K.E. and Keating, A., "Bead Transfection of Adherent Cells," *Mol. Biotech.* 5:259–261 (1996).

Partridge, S.M., "The State of Combination of Chondroitin Sulphate in Cartilage," *Biochem. J.* 43:387–397 (1948).

Partridge, T.A. and Davies, K.E., "Myoblast–based gene therapies," *British Medical Bulletin* 51(1):123–137 (1995).

Simoni, M. and Gromoll, J., "Monitoring the transfection efficiency of the human follicle–stimulating hormone receptor cDNA in COS–7 cells: evaluation of the growth hormone transient gene expression assay system," *J. Endocrinol. Invest.* 19:359–364 (1996).

Verma, I.M. and Somia, N., "Gene therapy–promises, problems and prospects," *Nature* 389:239–242 (1997).

SEQUENCE LISTING

```
<160> NUMBER OF SEQ ID NOS: 1

<210> SEQ ID NO 1
<211> LENGTH: 20
<212> TYPE: DNA
<213> ORGANISM: Escherichia coli

<400> SEQUENCE: 1

ctccaacgca gcaccatcac                                               20
```

STABILIZED TRANSIENT GENE EXPRESSION

This application is a continuation-in-part based on PCT patent application No. PCT/US97/19860, filed Oct. 31, 1997, which is a continuation-in-part based on U.S. patent application Ser. No. 08/833,747, filed Apr. 11, 1997, now abandoned, which U.S. Provisional Application 60/030,109, filed Nov. 1, 1996.

FIELD OF THE INVENTION

This invention relates to methods and agents that enhance the transient expression of foreign genes that have been introduced into cultured eukaryotic cells.

BACKGROUND OF THE INVENTION

The introduction of foreign DNA into eukaryotic host cells can serve many purposes. For example, this technique can provide a means of genetic complementation for identifying specific genes, e.g., a gene expressing an enzyme critical to a metabolic pathway can be identified by virtue of its ability to rescue cells defective in that pathway. Also, exogenous genes can be introduced for the purpose of exposing a recipient cell to a high dose of a protein not normally native to that cell, as for example, a cytotoxic protein introduced into a malignant cell for the purpose of killing it. Alternatively, foreign genes may be introduced into host cells to obtain the protein product of the foreign gene in sufficiently large amounts so that the protein can be harvested for further study or used as a pharmaceutical. In addition, the introduction of foreign genes is viewed as a promising avenue for somatic gene therapy. The goal of gene therapy is to cure inborn genetic defects by providing patients with a working copy of a missing or defective gene, or alternatively, to provide a therapeutic foreign gene product on a temporary basis for therapeutic purposes. One approach to somatic gene therapy is the ex vivo strategy, wherein cells are removed from the body, transgenic DNA is inserted into the cells, and the cells are then returned to the body. In another approach, cells in vivo are targeted by foreign DNA that is introduced directly into the patient. A variety of methods are available for introducing foreign genes into living cells.

Transfection protocols can be categorized as designed to produce "transient" or "stable" expression of the foreign gene. With currently available protocols, the line of demarcation between these two types of outcome is the integration of the introduced DNA into the host genome, and cells into which foreign DNA has become integrated are generally referred to as "stably transformed." In contrast to stable transformation, transient expression of transfected DNA does not depend on the integration of foreign DNA into host cell chromosomes. Although the majority of DNA applied to a cell is believed to be rapidly transported into the nucleus, in some systems expression can be detected for up to 80 hours post-transfection in the absence of any detectable integration (see, e.g., Gorman, C., *DNA Cloning II, A Practical Approach;* Glover, D. M., Ed., IRL Press, Oxford, pp. 143–190 (1985); Wynshaw-Boris et al., *BioTechniques,* 4:104–117 (1986)). No selection step is required before transient expression can be detected. However, only about 1–10% of cells that take up foreign DNA typically transcribe mRNA from unintegrated foreign genes (see, e.g., Gorman et al., *Nucl. Ac. Res.,* 11:7631–7648 (1983)). Although the vast majority of transfected DNA in transiently transfected cells does not become incorporated into the host DNA, it does become incorporated in about 0.001–1% of these cells (Alam and Cook, *Anal. Biochem.,* 188:245–254 (1990)). This small stably transfected fraction of cells is believed to play no significant or useful role in the foreign gene expression profile observed immediately after transfection. Protocols using viral vectors have been developed to increase the proportion of initially transfected cells that integrate the foreign DNA (Flamant et al., *Int. J. Dev. Biol.,* 38:751–757 (1994); Bilbao et al., FASEB J., 11:624–634 (1997)).

Without a selection step, the expression of foreign genes generally disappears from cultures of transfected cells within two to three days. Typically, expression peaks in about 48 hours, and is detectable for only 24–80 hours (Gorman (1985); Wynshaw-Boris et al., (1986); Berthold, W., *Dev. Biol. Stand.,* 83:67–79 (1994)). It is widely believed that most of the DNA taken up by transfected cells becomes rapidly catabolized by nucleases or becomes diluted by cell division (see, e.g., Gorman (1985); *Guide to Eukaryotic Transfection with Cationic Lipid Reagents, Life Technologies;* Bilbao et al. (1997)).

Because transient expression does not require that the target cells are actively dividing, it can be achieved in terminally differentiated cells that do not normally divide, although susceptibility to transfection varies dramatically among such cells. For example, naked DNA can be expressed over a long period of time when injected directly into mouse skeletal muscle (Wolff, et al., *Science,* 247, 1465–1468 (1990)). In other studies, naked DNA has been used as a vaccine (e.g., Cohen, J., *Science,* 259, 1691–1692 (1993)), and defective retrovirus vectors have been used to harness myoblasts as vehicles for delivering transgenic products (Partridge and Davies, *Brit. Med. Bull.,* 51:123–137 (1995)).

Many studies have focused on the liposomal delivery of foreign DNA in vivo to hepatocytes (see, e.g., Wu and Wu, *J. Biol. Chem.* 263:14621–14624 (1988); Chow et al., *J. Pharmacol. Exp. Ther.,* 248:506–13 (1989); Wu et al., *J. Biol. Chem.,* 264:16985–16987 (1989); Kaneda et al., *J. Biol. Chem.,* 264:12126–12129 (1980a); Kaneda et al., *Science,* 243:375–378 (1989b); Wilson et al., *J. Biol. Chem.,* 267:963–967 (1992a); Wilson et al., *J. Biol. Chem.,* 267:11483–11489 (1992b); Chowdhury et al., *J. Biol. Chem.,* 268:11265–11271 (1993); Perales et al., *Proc. Natl. Acad. Sci. USA,* 91:4086–4090 (1994); Kormis and Wu, *Seminars in Liver Disease,* 15:257–267 (1995); Buolo et al., *Mol. Marine Bid. Biotech.,* 5:167–174 (1996)). One approach to targeting foreign DNA to specific tissues in vivo is receptor-mediated liposomal delivery (reviewed in Kormis and Wu (1995)). In applying this strategy to liver, Wu and his colleagues exploited the presence of asialoglycoprotein receptors on hepatocyte surfaces to target injected liposomes to the liver. The liposomal delivery system is characterized in a number of publications (Wu and Wu (1988); Wu et al., (1989); Wilson et al., (1992a); Wilson et al. (1992b); Chowdhury et al. (1993); Perales et al. (1994)). The asialoglycoprotein was packaged into liposomes together with DNA that had formed an electrostatic complex with polylysine. When initial efforts were successful, this group attempted to maximize the stable integration of the foreign DNA by performing partial hepatectomies in the recipient rats. As regenerating liver cells provide a higher proportion of cells in S phase than are present in normal liver, this tactic was expected to increase the proportion of liver cells into which foreign DNA could integrate. After partial hepatectomy, the transgenic protein was detectable in the blood for as long as 11 weeks post-transfection (Wu et al. (1989)). At first, these investigators believed that the injected DNA had become integrated, but later experiments revealed no detectable integrated DNA, showing instead that the preserved foreign DNA resided in the plasma membrane/endosome fraction (Wilson et al. (1992b); Chowdhury et al. (1993)). This surprising observation indicated that partial hepatectomy leads to the persistence of transgenic DNA by a mechanism that is independent of DNA synthesis per se. Others have reported strategies for improving the transfection efficiency with a liposomal delivery vehicle by varying the ratio of DNA to lipids (Buolo et al. (1996)).

Another group also has employed a targeting strategy for directing injected DNA to the liver (Kaneda et al. (1989a); Kaneda et al. (1989b)). Here, transgenic DNA was packaged in liposomes with proteins normally found in the nucleus, i.e., non-histone chromosomal proteins. They observed transport of the injected vesicles to the nuclei of liver cells, and detected measurable transgene expression for up to 7 or 8 days after injection. However, this DNA did not become integrated into the liver cell chromosomes. Others have reported the successful in vivo expression of foreign DNA following the injection of $CaPO_4$-DNA precipitates directly into the liver, spleen, or peritoneum (see Kaneda et al. (1989a)).

A number of reagents have been shown to increase the efficiency in vitro of stable transformation. One group has reported that by controlling the pH in the culture medium during $CaPO_4$ mediated transfection, stable transformation efficiencies as high as 50% can be achieved (Chen and Okayama, *Mol. Cell. Biol.,* 7:2745–2752 (1987)).

Another reagent reported to enhance the expression of transfected DNA is butyric acid or its sodium salt (Gorman et al. (1983)). After exposing cells to sodium butyrate for 12 hours, Gorman et al. observed a 2–4-fold increase in the percentage of recipient cells expressing the transgene, as well as a 25–100-fold increase in the foreign gene expression levels when an SV40 enhancer was added to the construct. When other cultures transfected in the presence of butyrate were selected for stable transformants, they observed a significant increase over controls in the percentage of transfected cells that gave rise to stable transformants. However, Palermo et al. (*J. Biotech.,* 19:35–48 (1991)) observed that butyrate induced increased transgene expression in stable transformants whether or not it had been present during the transfection step. Indeed, many reports have documented butyrate's ability to induce the synthesis of certain proteins or to increase cell differentiation in vitro. (Boffa, et al., *J. Biol. Chem.,* 256:9612–9621 (1981); Kruh, *Mol. Cell. Biochem.* 42:65–82 (1982); Chabanas, et al., *J. Mol. Biol.,* 183:141–151 (1985); Parker, *J. Biol. Chem.,* 261:2786–2790 (1986); Kooistra, et al., *Biochem. J.,* 247:605–612 (1987); Kaneko, et al., *Canc. Res.,* 50:3101–3105 (1990); Nathan, et al., *Exp. Cell Res.,* 0:76–84 (1990); Palermo, et al. (1991); Kosaka, et al., *Exp. Cell Res.,* 2:46–51 (1991); and Oh, et al. *Biotechnol. Bioeng.,* 42:601–610 (1993)). Optimal concentrations of butyrate for gene induction vary from cell type to cell type, and a suitable concentration range that minimizes its cytotoxic effects must be empirically determined for each type of target cell (see, e.g., Gorman (1985); Parker et al. (1986); Oh et al. (1993)). Butyric acid (or butyrate) also has been reported to reversibly suppress the growth of cultured cells (Boffa et al. (1981)), and to enhance the antitumor action of interferon (Kruh, 1982).

The usefulness of transient expression, i.e., expression from unintegrated foreign DNA, would be greatly improved if methods and reagents were available for increasing the efficiency and duration of transgene expression in the absence of selection steps.

SUMMARY OF THE INVENTION

This invention provides methods and agents that significantly enhance the expression of foreign DNA that has been introduced into a host eukaryotic cell. The agents described herein increase the efficiency, the amount and the duration of transient expression without requiring a selection step. The chemical compounds that comprise these agents are demonstrated to be efficacious in both growing cells and in static culture of non-dividing cells. The enhanced transgene expression induced by these compounds does not involve integration of the foreign DNA into the genome of the recipient host cell.

Furthermore, it is shown here that the compounds of this invention depress the consumption by cultured cells of glucose present in the culture medium, thus forcing the cells to rely for energy on alternative carbon sources. These same cells exhibit an increased production of ammonia, thus suggesting that protein is being used as an alternative source of energy. In addition, cells grown in the presence of these compounds are induced to express and secrete an endogenous alkaline phosphatase activity.

The invention further provides long-term transient expression of foreign genes that have been introduced into target cells by a variety of delivery systems, including but not limited to cationic lipids (i.e., liposomes) and various synthetic polymers such as dendrimers (also known as "starburst" polymers; e.g., see U.S. Pat. No. 5,661,025). Many of the subject chemical compounds influence the fate of foreign gene expression well after the foreign DNA has been introduced into the cell, thus act independently of the method by which the DNA is introduced. Some of the subject compounds are especially effective in increasing the degree of expression during the first four days following the introduction of foreign DNA, thus appear to enhance the initial amount of DNA taken into the cells, and/or to increase the proportion of cells that express the DNA, while others of the compounds prolong the duration of transient expression.

The compounds of this invention have a hydrophobic moiety and an acidic moiety, and the latter may take the form of a salt or an ester. Moreover, they are biocompatible, i.e., when applied to cells at concentrations useful for enhancing transient expression, greater than 50% of the cells remain viable.

The methods of the subject invention involve categorizing the compounds into "Type A" formulations, which primarily increase the degree of transient expression during the first four days after foreign DNA is added to the cells, and "Type B" formulations, which primarily stabilize transient expression after the foreign DNA has entered the cell. In one preferred embodiment of the invention, expression is obtained by treating cells with a Type A compound or formulation before, during, and after the transfection step, and by further adding a Type B compound or formulation within hours or days (e.g., within 12–60 hours) after introducing the foreign DNA, and leaving it is contact with the cells thereafter. The period before and during the transfection step is called the "first phase of transient expression," and the period following the entry of foreign DNA into the target cells is called the "second phase of transient expression." At least one Type A compound usually is maintained in the medium throughout both phases of transient expression. The invention also provides an assay for determining the efficacy of individual chemical compounds and further provides formulations of two or more compounds for their use in both phases of transient expression.

The chemical compounds of the subject invention result in living cells being able to sustain the transient expression of foreign DNA for periods far longer than previously observed. Moreover, following the addition of these compounds, cultured cells surprisingly reduce their consumption of glucose, and concomitantly increase their use of alternative energy sources, such as proteins and possibly lipids.

In other embodiments, this invention provides methods for culturing hepatocytes in the absence of feeder cells and without the need to pre-coat cell culture substrata with proteinaceous or other adhesion-promoting molecules.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 graphically depicts the amount of cell growth for some of the plates described in Example 4 and Table 7. The numbers in the inset boxes of FIG. 1 correspond to the plate numbers listed in Table 7;

FIG. 5A indicates the concentration of ammonia measured in each sample;

FIG. 5B indicates the concentration of glucose measured in each sample; and

FIG. 5C indicates the concentration of lactate measured in each sample.

DETAILED DESCRIPTION OF THE PREFERRED EMBODIMENT

Figure 1:
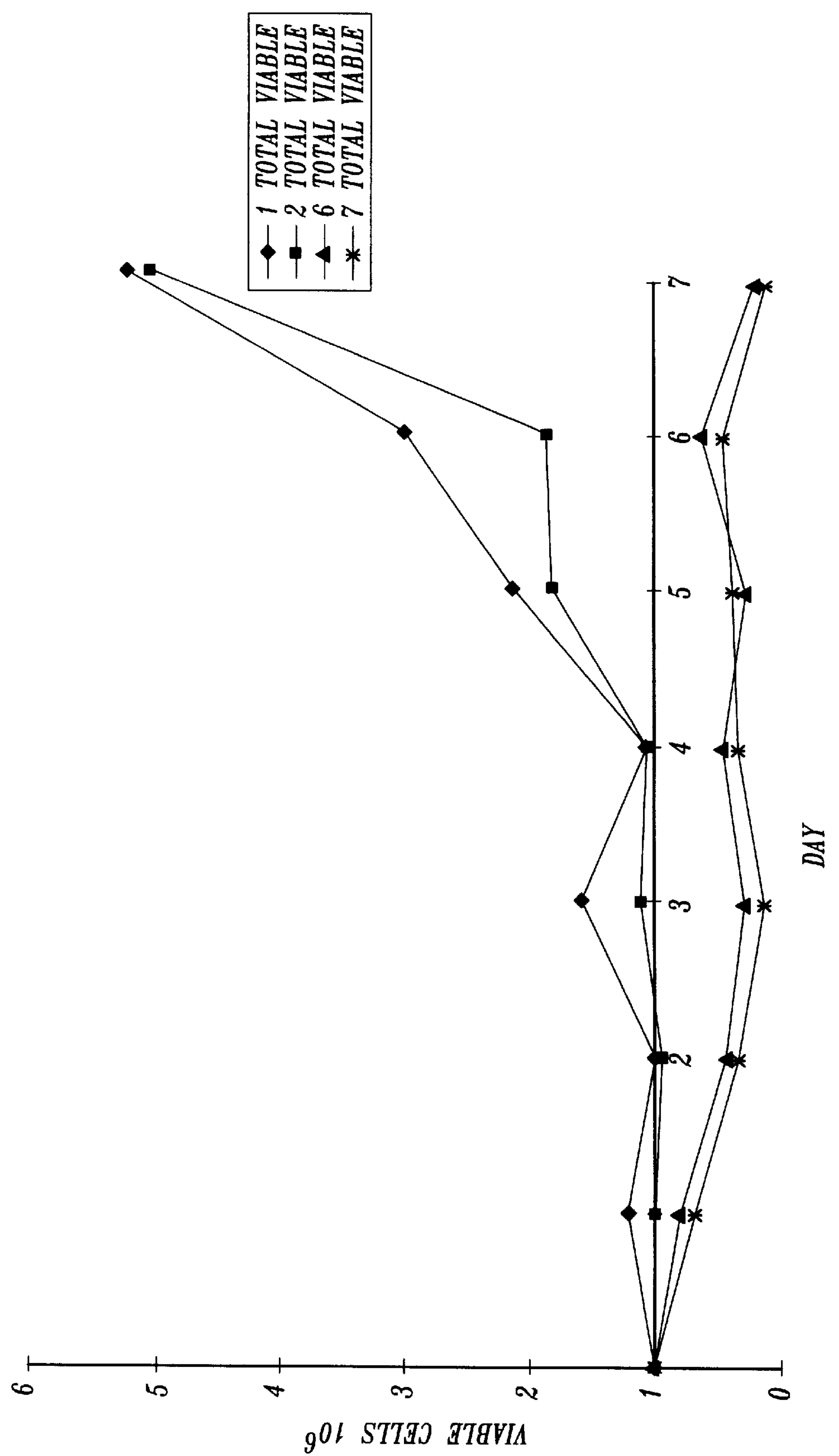
FIG. 1 shows a cell growth curve for cells exposed to several different compounds of the subject invention.

There are many advantages in using transient expression rather than stable transformation for the expression of foreign genes. First, by using transient expression, one can quickly analyze a relatively large number of constructs. Also, it may be the method of choice for delivering therapeutic proteins whose presence in the body is desired for the duration of the disease. Furthermore, transient expression avoids the danger of mutagenesis or cell death that may occur as the result of standard stable transformation protocols in which foreign DNA may become inserted into a critical cell gene. In addition, transient expression can be achieved in primary cell lines that are not immortalized, whereas stable transformants can be established only from cells that can survive and divide in cultures for long periods of time. However, with the exception of the liver hepatectomy model, a major drawback of currently known transient expression methods continues to be the relatively short-lived expression of the foreign gene, and the tendency of transfection reagents, including purified DNA itself, to be toxic to living cells. Moreover, hepatectomy or other surgical excisions are too drastic an approach for most practical purposes. Thus, the subject invention provides means for stabilizing transient expression that widen the applicability of this approach.

Definitions

Transfection: The term "transfection" refers here to any means of introducing foreign DNA into a recipient cell, including liposome-mediated methods, viral vectors, $CaPO_4$-DNA coprecipitates, DEAE-dextran, naked DNA, DNA complexed with proteins transfection in the presence of starburst polymers (dendrimers), or other means of introducing the DNA into the recipient cell.

Foreign DNA/transgenic DNA: Genetic material that has been appropriately prepared for expression in recipient eukaryotic cells, typically but not necessarily originating from an organism other than the recipient cell. Transgenic DNA typically will contain the coding region for a biologically active protein or protein domain (transgene). The transgenic DNA usually is in circular form and may be linked with a eukaryotic promoter or other regulatory signals to direct functional transcription of the foreign gene in the host cell. Regulatory signals may include a promoter for binding RNA polymerase, an enhancer, transcription termination signals, ribosome binding sites, translation start and stop signals, poly(A) addition signals, and so on. The enhancer may be tissue-specific or inducible, and signal peptides that direct the secretion of the transgenic protein may be positioned in the construct to produce a fusion protein that is secreted into the culture medium.

β-galactosidase (β-gal): A bacterial enzyme able to convert a colorless substrate into an easily detectable colored product. This gene is used in the Examples described below as a representative foreign gene for demonstrating the efficacy of this invention.

"Transfection" or "transduction" describe the process by which foreign genes ("transgenes") are introduced into a living host cell. Host cells that express or incorporate the foreign DNA are known as "transformed cells," and the process by which they become transformed is called "transformation" or "transduction." Different types of cells vary in their susceptibility to transformation, and protocols for introducing the foreign DNA are typically optimized by the adjustment of various parameters such as pH, type of culture medium, amount of DNA, $CO_2$ concentration, or method of DNA introduction (see, e.g., Chen and Okayama, *Mol. Cell. Biol.,* 7:2745–2752 (1987); Buolo et al. (1996)).

The subject methods and agents for enhancing the transient expression of foreign genes are efficacious in a variety of eukaryotic cells, e.g., tumor cell lines, differentiated cells, and non-immortalized primary cells. Specific cell types in which efficacy has been demonstrated include human colon carcinoma cells, mouse melanoma cells, porcine primary hepatocytes, and in a porcine cell line that resembles differentiated hepatocytes.

For either transient or stable transfection, the foreign DNA may be introduced into the cell by any convenient method, including but not limited to, lipofection, electroporation, incubation with $CaPO_4$-DNA coprecipitates, glass beads, incubation with DEAE-dextran, ligation of the DNA into a viral vector, and so on. For lipofection, the DNA is associated with liposomes, which are liquid-filled sacs formed by lipid molecules that aggregate to form a membrane structure. DNA molecules can become encapsulated in liposomes or can be associated with liposomal membranes. The liposomes are fused with recipient cells as a means of introducing foreign genes into the cells. Although widely used, one limitation of lipofection is that liposomes are somewhat toxic to living eukaryotic cells. In other commonly-used methods, DNA can be co-precipitated with $CaPO_4$ before being applied to cells, or the entry of foreign DNA can be mediated by DEAE-dextran, a polymer that forms an electrostatic complex with DNA, the complex being internalized into cells by endocytosis (Kormis and Wu, *Seminars Liv. Dis.,* 15:257–267 (1995)). Exemplary transfection protocols are widely available (see, e.g., Sambrook et al., *Molecular Cloning,* 2d ed., (1989), which is hereby incorporated by reference; Gorman, C., Chap. 6, pp. 143–190 from *DNA Cloning II—A practical Approach,* IRL Press, Oxford (1985), Ed. Glover, D. M.; Wynshaw-Boris et al., *BioTechniques,* 4:104–119 (1986); Chang, P. L. (Ed), *Somatic Gene Therapy,* CRC Press, 1995; and *Guide to Eukaryotic Transfection with Cationic Lipid Reagents,* Life Technologies (Gibco-BRL); Matthews and Keating, *Molec. Biotech.,* 5:259–261 (1996)). Electroporation is used also, which involves the entry of foreign DNA into cells in response to a brief high voltage electrical pulse (e.g., see Barsoum, J., *Methods in Molecular Biology,* 48:225–237 (1995)).

When foreign DNA is introduced into cells in the form of a $CaPO_4$ co-precipitate or using DEAE-dextran, it was observed in the past that most of the cells initially take up the DNA, but only a fraction of them express the DNA after it has been introduced (see, e.g., Gorman (1985)). Expression of transfected DNA using previously available protocols is typically short-lived. A still smaller fraction of the recipient cells (0.1–0.001%) will stably incorporate the transfected DNA by covalently linking it into the host genome (see, e.g., Wynshaw-Boris et al. (1986)). A likely reason for the observed low level of covalent integration is that active DNA synthesis must occur in order for integration of the foreign DNA to take place. Thus, cells generally are considered to be susceptible to stable transformation only during the S phase of the cell cycle. However, as only a tiny fraction of the cells in a transfected culture typically contain integrated foreign DNA, the amount of transgenic protein expressed from stably transformed cells is small, or even undetectable. Accordingly, stable transformation protocols generally rely on a post-transfection selection step to increase the proportion of stably transformed cells (e.g., Kelleher and Vos (1994)). When conventional transfection protocols are used, transient expression typically decays to an undetectable level within 2–3 days after the foreign DNA has been introduced into the cells unless the cells are cultured after transfection in a selective culture medium that provides a growth advantage to cells that have stably integrated the transfected DNA, or otherwise facilitates the detection and cloning of those cells containing integrated DNA (e.g., Gorman (1985); Buolo et al. (1996)).

Homogenous cultures of stably transformed cells can be selectively isolated under a variety of experimental conditions to obtain lines of cells that have integrated the foreign gene, and that continue to express it. Typically, a selectable gene, e.g., one that confers drug resistance or encodes a chromogenic protein, is introduced into the host cell concurrently with DNA that encodes the desired protein. Examples of reporter genes suitable for this purpose include bacterial chloramphenicol acetyltranferase, luciferase, alkaline phosphatase, bacterial β-galactosidase, and others (see, e.g., Alam and Cook, *Anal. Biochem.,* 188:245–254 (1990)). If a drug-resistance marker is being used, drug resistant cells must be exposed to the relevant drug for several weeks in order that the stably transformed cells can become predominant in the culture. Alternatively, cells containing integrated DNA may be identified by their expression of a co-transfected gene that is capable of converting a chromogenic substrate into a colored substance that permits the identification and manual cloning of individual stably transformed cells. In rare instances, the desired gene itself may confer a selectable trait on the stably transformed cells. In any case, the creation and isolation of stably transformed cell lines can take one to three months to accomplish. (Wynshaw-Boris et al. (1986)). In contrast, cells transfected according to the subject methods are cultured after the transfection step in a non-selective medium, i.e., a medium free of drugs that selectively kill cells lacking the transgenic protein, and that employs no chromogenic or other means to distinguish or to physically separate cells containing foreign DNA from cells that have not integrated the DNA. Yet, using the subject methods, cells continue to express detectable amounts of transgenic protein far beyond the 80 or so hours expected with conventional methods. Using the subject methods, DNA and RNA homologous to transfected foreign DNA is detectable 4–5 days post-transfection, and as much as 32 days post-transfection. When the subject methods are applied, transient expression typically peaks within about 2–3 days, then declines to a level of about one-third the initial level, and thereafter remains stable for several days to several weeks, though this pattern may vary, depending on which agent or agents are used. Thus, an especially advantageous feature of the invention is that it provides relatively long-term transient expression without requiring the lengthy selection steps used for establishing cultures of stably transformed cells.

In one embodiment of the invention, the foreign protein is detected after cells transfected in accord with the invention have been maintained for at least four days in a non-selective medium. The non-selective medium may be tissue culture medium, or if the transfected cells are present in a live host, may be blood, plasma, or extracellular fluids. For purposes of this and all other embodiments of the disclosed invention, it is understood that the "agent" is a chemical compound other than an expression vector or the transgenic DNA itself. On removal of the chemical compounds from the cell culture media, transgene expression gradually disappears and the previous behavior of the cell resumes.

Vectors derived from retroviruses or adenoviruses are useful for introducing foreign DNA into eukaryotic host cells (see, e.g., Verma and Somia, *Nature,* 389:239–242 (1997)), which normally do not integrate, though most viral vectors are effective only in actively dividing cells. Adenoviruses have been shown to be particularly efficient for use in transient expression (e.g., Kelleher and Vos (1994)). If desired, the plasmid or viral vector containing the foreign DNA may provide nucleotide sequences positioned between the promoter and the insertion site, or alternatively, positioned following the insertion site, such that one or more amino acids encoded by the vector-provided nucleotide sequences become fused to the protein encoded by the foreign DNA. Such fusion sequences can provide peptides that direct desired post-translational modifications, such as signal peptides for secretion, or sites for attachment of carbohydrate moieties.

For transient expression in accord with the present invention, before, during, or after the introduction of the foreign DNA into a cell, the cell is contacted with one or more of the chemical compounds described below, whereafter the expression of the foreign DNA is substantially enhanced as compared with cells transfected in the absence of these compounds. By "enhancing transient expression," it is meant here that when the subject methods are used, the amount of transgene expression during the first few days following transfection is increased as compared with controls, or that the period during which transient expression occurs is prolonged as compared with controls, or both. For these methods, transfected cells are contacted with one or more chemical agents that increase the efficiency of initial DNA uptake or expression, or that prolong the effective half-life of the foreign DNA after it has entered the cell. Individual compounds may exert both of these effects. The "effective half-life of the foreign DNA" is determined based on measurements of the amounts of transgenic protein present in culture samples rather than direct measurements of the amounts of transgenic DNA.

Specific agents useful for the subject methods include a large number of chemical compounds that are characterized more fully below. An "agent" may consist of a single chemical compound, or a combination of two or more compounds. Moreover, the agent may include one or more compounds administered during the first phase of transient expression, and an additional compound or compounds added after the foreign DNA has entered the cell. These transient expression enhancing agents may be present before, during, and after the introduction of foreign DNA. When added to the cells after introducing the DNA, the agent typically remains in contact with the cell for at least 24 hours, or longer.

Chemical compounds useful as agents for the subject methods include at least one hydrophobic moiety and at least one acidic moiety. Even a mildly hydrophobic moiety, e.g., one having a two carbon chain, can impart sufficient hydrophobicity for the purposes of this invention. The acidic and hydrophobic moieties may reside in a single agent, e.g., a molecule that is both hydrophobic and organic. For certain of these chemical compounds, the acidic moiety is modified as a salt or an ester. In one embodiment, the chemical compounds are carboxylic acid derivatives represented by the general formula $R_1$—C(═O)—$OR_2$, and in another embodiment, the chemical compounds are sulfonic acid derivatives represented by the general formula $R_7$—$SO_2$—$OR_8$.

Suitable carboxylic acid derivatives (i.e., $R_1$—C(═O)—$OR_2$) include naturally occurring amino acids (e.g., glycine, alanine, valine, leucine, isoleucine, aspartic acid, glutamic acid, glutamine, serine, threonine, methionine, arginine, lysine, histidine, proline, tryptophan, phenylalanine, tyrosine), their unnatural optical isomers, and certain amino acid derivatives (e.g., 3-methyl-L-histidine, α-ketoglutaric acid, β-alanine, carnosine, citrulline, creatine, folic acid, glutathione, hippuric acid, homoserine, N-carbamyl aspartic acid, N-formyl-L-methionine, and ornithine).

Referring to the general carboxylic acid derivative formula, $R_1$—C(═O)—$OR_2$, for the amino acids, $R_1$ is $CHNH_2R_3$, wherein $R_3$ is the side chain of a naturally occurring amino acid. Other amino acid derivatives that are useful in the method of the present invention include amino acids that further include alkyl substituents and alkyl substituents having additional functional groups. These amino acid derivatives are represented by the above carboxylic acid derivative formula where $R_1$ is —$CHNH_2(CH_2)_nR_5$, wherein n=1–7 and $R_5$ is selected from $CH_3$, OH, $CONH_2$, $C_6H_4OH$, and $CONHNH_2$. Alternatively, $R_1$ is —$(CH_2)_nCHNH_2CO_2H$, wherein n=1–8; —$CH(CO_2H)NHCONH_2$, or $R_1$ is —$C_5H_4N$ (i.e., nicotinic acid and derivatives).

In addition to amino acids, the carboxylic acid derivatives useful in the present method include alkyl, aryl, and substituted alkyl and aryl carboxylic acid derivatives. Preferred alkyl and substituted alkyl carboxylic acid derivatives are represented by the general formula above where $R_1$ is —$(CH_2)_nR_6$, wherein n=1–9 and $R_6$ is selected from an indole group, $NCH_3C(═NH)NH_2$, $SCH_3$, $NH_2$, $CH_3$, $CO_2H$, $CONH_2$, and $NHC(═NH)NH_2$. Preferable aryl carboxylic acid derivatives include benzoic acid and its derivatives. The benzoic acid derivatives are represented by the formula above where $R_1$ is —$C_6H_4R_4$, wherein $R_4$ is selected from H, $CH_3$, $(CH_2)_nCH_3$, $NH_2$, $COCH_3$, $CO(CH_2)_nCH_3$, $C(CH_3)_3$, $CH(CH_3)_2$, $(CH_2)_nCH(CH_3)_2$, $(CH_2)_nCOCH_3$, $OCH_3$, and $O(CH_2)_nCH_3$, wherein n=1–3. It has been found that branched chains often are more efficacious than linear drains.

The carboxylic acid derivatives useful in the present invention include carboxylic acids (i.e., $R_2$ is H); carboxylic acid esters (e.g., $R_2$ is $CH_3$ and $(CH_2)_nCH_3$ wherein n=1–8) including esters having additional functional groups such as ether and ketone groups (e.g., $R_2$ is $(CH_2)_xO(CH_2)_yCH_3$ and $(CH_2)_xCO(CH_2)_yCH_3$ wherein x+y=2–7); and carboxylate salts including metallic salts (e.g., lithium, sodium, potassium, calcium, and magnesium) as well as relatively low molecular weight cations (e.g., ammonium).

Suitable sulfonic acid derivatives, represented by the general formula $R_7$—$SO_2$—$OR_8$, include alkyl, aryl, substituted alkyl and aryl sulfonic acid derivatives (i.e., $R_7$ is an alkyl, aryl, or substituted alkyl or aryl group). Preferably, the sulfonic acid derivative is a lower alkyl (i.e., straight chain or branched $C_1$–$C_5$ alkyl group) sulfonate, and more preferably, an amino substituted lower alkyl sulfonate, for example, taurine. Preferably, the aryl sulfonic acid derivatives is a benzene sulfonic acid derivative, and more preferably, an amino substituted benzene sulfonate, for example, 3-aminobenzene sulfonic acid. The sulfonic acid derivatives useful in the present invention include sulfonic acids (i.e., $R_8$ is H), and sulfonic acid salts including metallic salts (e.g., $R_8$ is lithium, sodium, potassium, calcium, or magnesium) as well as relatively low molecular weight organic cations (e.g., $R_8$ is ammonium ion).

In another embodiment, the chemical compounds useful as agents in the subject methods include polysaccharides, including both naturally-occurring polysaccharides, e.g., those derived from plant and animal sources, which often occur naturally in a carboxylated form, or which may be carboxylated using standard chemical procedures. For example, chitin or cellulose may be carboxylated using standard chemical methods.

Polysaccharides useful for the subject invention include the glycosaminoglycans, which are linear polymers with repeating disaccharide units that contain one hexosamine and either a carboxylate or sulfoester, or both (for review, see Hascall et al., *Methods in Enzymology* 230:390–417 (1994)). There are four types of naturally-occurring glycosaminoglycans: (i) hyaluronic acid; (ii) chondroitin sulfate and dermatan sulfate; (iii) keratin sulfate; and (iv) heparin sulfate and heparin. The latter three types in their natural state are proteoglycans, i.e., they are covalently attached to protein chains. These must be deproteinized before they are effective for the subject methods. The deproteinization can be accomplished by any convenient means, e.g., by heating in alkali such as KOH or NaOH (Bray, et al., 1944; Partridge, S. M., *Biochem J.* 43:387–397 (1948)).

Especially useful compounds for the subject invention are the sulfonated amino polysaccharides. Naturally occurring amino polysaccharides that do not normally contain sulfur, e.g., hyaluronic acid, or the guarans, can be modified using standard chemical reactions, e.g., by heating in the presence of sulfuric acid. Preferably, the polysaccharide is a sulfonated N-acetylated amino polysaccharide. Polysaccharide agents are generally most effective in enhancing transient expression if added after the transfection step.

The effectiveness of a preparation of sulfonated N-acetylated amino polysaccharide for use in the subject invention varies with the size of the polymer. Suitable polysaccharides typically contain from about 1 to about 50 repeating units, preferably 1–20 repeating units, or more preferably, 1–10 repeating units, the repeating units usually comprising a disaccharide. Thus, preferred sulfonated N-acetylated amino polysaccharides have an average molecular mass of no greater than 20 kDa, or more preferably no greater than 9 kDa, and most preferably, no greater than 4 kDa. Sulfonated amino polysaccharides extracted from natural sources usually consist of polymers of 20 kDa or greater, but methods well known in the art can be used to fragment large polymers into polymers of a smaller and more suitable size. Such methods generally involve heating the polymer first in an alkaline solution, then in an acidic solution (e.g., Bray et al., *Biochem. J.* 38:142, (1944)). Heating in sulfuric acid will suffice to both sulfonate and fragment a polysaccharide chain. It should be understood that preparations of polysaccharides are not uniform in size, and a size assigned to a preparation of polysaccharide is only approximate. The average molecular mass of a polysaccharide preparation can be determined electrophoretically, using methods known in the art, e.g., Partridge, S. M., (1948). By "average molecular mass," is meant the size of the polymer at the peak or mean value that is observed in the electrophoresis tracing, or the average value observed using other size-determination analysis methods.

Preferred sulfonated N-acetylated amino polysaccharides include chondroitin sulfate, heparin, and dermatan sulfate. Chondroitin sulfate is naturally-occurring constituent of connective tissue, and generally is purified from extracts of cartilage. It varies in its molecular weight, degree of sulfonation at the N-acetylgalactosamine residue of the repeat disaccharide, and in the relative distribution of sulfated to unsulfated repeat units. Commercial preparations of chondroitin sulfate typically contain variable proportions of chondroitin-6-sulfate ($C_6$) and chondroitin-4-sulfate ($C_4$). "Type A" chondroitin sulfate preparations generally contain 30% of the $C_6$ isomer, and 70% of the $C_4$ isomer, while "Type C" preparations of chondroitin sulfate generally contain 10% $C_4$ and 90% $C_6$. Both Type A and Type C chondroitin sulfate preparations are available, for example, from Sigma, or from Biorelease Corp. For example, Biorelease Corp. offers several Type A preparations; No. 409-4U (4 kDa); No. 409 (9 kDa); and No. 4D36 (>20 kDa). Both Type A (predominantly $C_4$) and Type C (predominantly $C_6$) preparations are effective for enhancing transient expression.

Preferred polysaccharides include the guarans, which are isolated from the endosperm of *Cyamopsis tetragonolobus* seeds as high molecular weight β-1,4 D-galactomannans (e.g., up to about 1,200,000 daltons) having α-1,6-linked D-galactose residues attached to a mannan backbone. Guarans suitable for the disclosed methods include 2-hydroxypropyl ether derivatives commonly referred to as hydroxypropyl guarans. Commercially available preparations of guarans can be rendered more effective for enhancing transient expression by first being subjected to fragmentation and sulfonation. This can be accomplished, for example, by heating the guaran in sulfuric acid.

Other chemicals compounds that are useful in the method of the present invention include adrenaline (epinephrine), coenzyme B12, and methylcobalamin.

Chemical compounds effective in enhancing transient expression have the following desirable characteristics in common:

1. Little or no cytotoxicity when added to cells in culture within concentration ranges effective for enhancing transient expression. For the polysaccharide agents, this range is about 0.01–0.5 mM. For the remaining compounds effective in enhancing transient expression, this range is about between 1–15 mM. These optimal amounts are in addition to quantities of these substances that may already be present as a cell culture media component (e.g., certain amino acids). Compounds that are not cytotoxic according to this assay are defined here as "biocompatible." For the purposes of this invention, a cytotoxic substance may be defined as one that, at a given concentration, results in >50% decline in the number of viable cells within 4 days post-transfection in an 8 day static culture of SW480 cells, with continuous exposure to the substance, and wherein no net expansion of the cells occurs by the end of the 8-day period. However, it should be understood that various types of cells vary in their sensitivity to different chemical compounds. Thus, while SW480 cells may be used as a convenient tool for determining biocompatible concentrations of the chemical compounds, it may be necessary to empirically adjust the concentrations determined with SW480 cells in order to optimize biocompatibility with other types of cells. Assays for cytotoxicity are described in greater detail in Example 4.
2. An anionic functional group, usually an acid, is always present (e.g., carboxylic, sulfonic, and the like), and may be modified to reduce cytotoxicity. Preferred modifications are ester and salt formation (including salt based on organic cations), as salt and ester bonds are readily cleaved by metabolic processes after the compound has entered the target cell. In a preferred embodiment, the chemical compound in aqueous solution has a pH of 4.5–10.5.
3. In addition to the anionic group, the molecule contains a relatively hydrophobic organic group. For compounds other than the sulfonated polysaccharides, this portion of the molecule is preferably non-polar and hydrophobic. Similarly, the sulfonated polysaccharides have their natural hydrophilic character modified by the presence of a relatively hydrophobic functional group (e.g., the N-acetyl group in chondroitin sulfate in the 2-substitution position, is a modified amino group, which is relatively hydrophobic as compared with an unmodified amino group). Many of the compounds that have proven efficacious for the subject invention contain an acidic group that is organic and hydrophobic.
4. Several of the most effective agents (e.g., a 50/50 mixture of benzoic acid and sodium benzoate (benzoate buffer), and chondroitin sulfate) possess antioxidant and free radical scavenging character (e.g., see Merck Index).

Hereafter, the compounds other than the sulfonated amino polysaccharides will be referred to as "Group I," while the polysaccharide agents will be called "Group II." In a preferred embodiment of the invention, the cells are contacted with a chemical compound selected from Group I prior to and during the introduction into the cell of the foreign DNA (i.e., the transfection step), and are further contacted with a chemical compound selected from Group II following the introduction of the foreign DNA. Group I compounds are efficacious whether they are added to the cells prior to, during, or after the transfection step, whereas Group II compounds are most effective when added after the cells have taken up the foreign DNA. Group I compounds most preferably are present before, during and after adding the DNA to the cultures.

It should be noted that some variability has been observed in different experiments in which the same compounds were used to enhance transient expression. In instances where a lower-than-expected degree of enhancement was observed, this phenomenon was correlated with the detection of high levels of endotoxin in the transfection solutions using the LAL assay described in Example 10 to measure endotoxin levels. Accordingly, it is advisable to minimize endotoxin contamination by preparing all transient expression solutions under conditions that minimize the presence of bacteria, e.g., by preparing the solutions in a hood under standard aseptic conditions. Using such conditions, LAL levels of 0.015 to 0.06 were routinely obtained (see Table 12), which levels are well below the 0.25 Eu/ml maximum permitted for water for injection under FDA guidelines. The upper limit for endotoxin levels at which enhanced transfection will occur has not been determined, but in one experiment, enhanced transient expression was observed using a solution that contained 0.24 Eu/ml. Thus, the upper limit appears to be >0.24 and may lie between 0.5 and 1.0 Eu/ml.

The subject invention provides methods useful for prolonging transient expression in cultured cells, including primary cultures, established cell lines, stable cultures of differentiated cells, normal cell lines maintained by exposure to growth factors, and transformed cells, such as cultures established from various tumors, including hybridoma cells and the SW480 P3 human colon carcinoma cell line (ATCC #CCL228; hereafter referred to as "SW480 cells"). Examples of particular cell lines for which the subject methods are effective include IB-3 cells (a human bronchial epithelial cell line); ATCC No. BP6-FO cells (mouse melanoma); PIC M-19 (porcine epiblast-derived hepatic stem cell-like cells; COS-7; CHO-K1; human melanoma cell line.

The subject methods are useful also for introducing foreign DNA into cells in vivo. The compounds can be administered by any convenient means, including orally, topically, by perfusion, by injection, or by aerosol delivery to the lungs. If it is desired to confine the host's exposure to the chemical compound to the tissues that will receive foreign DNA, the chemical compound can be introduced by localized injection, such as, for example, injection directly into a solid tumor mass, or by incorporating into liposomes a protein that targets them to specific tissues, or by incorporating them into a slowly-degrading semi-solid biocompatible polymer. Injections of the chemical or combination of chemicals can be accompanied by or followed by injection at the same site of a vehicle for delivering the foreign DNA. Alternatively, the compounds can be applied in a vehicle that provides for the slow release of the compounds at the target site, as, for example, by the dissolution of an inert solid biocompatible carrier. In addition, the subject compounds can be co-administered with naked DNA vaccines, to thereby increase their effectiveness.

The subject invention contemplates the harvesting or detection of proteins expressed by the transgenic DNA introduced into cells in the presence of the above-described compounds. The protein can be harvested by any convenient means, such as, for example, by extracting the transfected cells, or by extracting the culture medium in which the cells are grown, e.g., in cases where the foreign protein is designed to include a signal peptide for secretion. The purification procedure used for a given protein will depend on the physical properties of the protein, such as its size, shape, hydrophobicity, stability, and so on. The harvested protein may be detected or quantified by physical means, such as, for example, gel electrophoresis, isoelectric focusing, or by chromatographic methods such as high-pressure liquid chromatography, or the like. Transgenic protein also can be assayed repeatedly over a period of days to monitor the relative or absolute amounts of protein produced, thus providing a means for evaluating the effectiveness of variations in the transfection protocol or the effectiveness of compounds being tested to assess their ability to enhance transient expression. Crude cell extracts can be assayed for enzymatic or other biological activity of the harvested protein, or the protein can be further purified using standard procedures before performing functional assays for the protein's activity. If the transgene is expressed in vivo, the protein can be harvested from body fluids of the host, such as milk, or other body tissues.

The methods of the subject invention result in the rapid production in cultured eukaryotic cells or in transiently expressing mammalian hosts of useful quantities of the protein encoded by the transgene. For transgenes of eukaryotic origin, expression in eukaryotic cells is especially advantageous in that such host cells can support splicing and post-translational modifications. Moreover, proteins harvested from eukaryotic host cells are less likely than those harvested from bacterial hosts to contain toxic contaminants.

The subject methods provide a means for obtaining commercially useful amounts of a biologically active protein, e.g., a growth factor, hormone, antibiotic, and the like, from transfected eukaryotic host cells without a post-transfection selection step and without the establishment of a permanent cell line containing stably integrated foreign DNA. These methods can be scaled up for rapidly obtaining biologicals to be tested for their pharmaceutical properties.

Contacting cells with the chemical compounds selected from Group II of the subject invention results in increased cell adhesion and cell-to-cell contact and communication, thus administration of these compounds provides a means for enhancing these cell-cell interactions. Thus, the subject invention includes methods for enhancing the adhesion of a cell to a culture substratum by growing the cells in the presence of a sulfonated amino polysaccharide that has been added to the culture medium, thus promoting the longevity of the cells in culture. Hepatocytes, for example, will not survive ordinarily in culture unless feeder cells are provided or the culture substratum is first coated with a substance to promote hepatocyte adhesion (see, e.g., Sidhu and Omiecinski, *Pharmacogenetics,* 5:24–36 (1995)). However, chondroitin sulfate was effective in promoting the long-term growth in culture of a cell line that has the characteristics of differentiated hepatocytes. Chondroitin sulfate bonded to the surface substratum has been proposed previously as useful for providing a cell adhesive surface in a device for controlling the pattern of cells on a surface (U.S. Pat. No.

5,593,814). Others have reported using chondroitin sulfate in conjunction with other compounds in order to promote cell adhesion in culture or in vivo (U.S. Pat. No. 5,593,814; U.S. Pat. No. 4,458,678; U.S. Pat. No. 4,418,691; U.S. Pat. No. 4,711,780; U.S. Pat. No. 5,545,722).

When agents of the subject invention are contacted with cultured cells, the cells exhibit altered metabolic processes, including glucose consumption and lactate production, as well as increased ammonia production. Thus, the subject methods are useful for manipulating the metabolism of a cell such that the cell utilizes alternative carbon sources such as amino acids and peptides, or even possible lipids. An agent especially useful for manipulating a cell's utilization of energy sources is a combination of benzoate acid, 4-ethylbenzoic acid, chondroitin sulfate, and benzoate buffer, wherein benzoate buffer is an equimolar mixture of benzoic acid and sodium benzoate. The subject methods are useful for manipulating cell metabolism either in vitro or in vivo, e.g., to treat mammals for obesity.

Also, compounds of both Groups I and II induce cells to express elevated levels of an endogenous phosphatase activity that is detectable using a standard alkaline phosphatase assay. The amount of this phosphatase measurable in transfected cells appears to increase, or spike, just before the transgenic gene product begins to disappear from a transfected culture. Thus, periodic measurement of this phosphatase activity provides a means of monitoring transgene expression in transfected cultures, so that a decline in transgene expression can be anticipated.

The subject invention provides agents for enhancing transient expression both in vitro and in vivo. Optimally, the compounds are administered before, during, and after the introduction foreign DNA, and Group II compounds are administered after the introduction of foreign DNA. When employed in vivo, Group I compounds may be injected as a primer into the recipient tissue or intravenously admixed with the transgenic DNA solution, and administered after introduction of foreign gene by injection, or may be administered as a dietary supplement. For example, a tumor could be primed by direct injection of a chemical compound followed by later injection of the DNA, followed still later by an oral supplement of the same or different compounds.

In other embodiments, the invention provides methods for obtaining stabilized transient expression of foreign genes in cells grown in a bioreactor, i.e., a culture system that perpetuates cells in semi-solid masses that simulate solid tumors. Protocols developed in this model tumor system can be used to transfect genes expressing anti-tumor compounds, e.g., IL-2, directly into solid tumors, and as a test system for determining the efficacy of new anti-tumor drug candidates.

Group I and Group II compounds appear to act through different mechanisms to enhance transient expression, since combinations of compounds from the two groups are often more effective than when the compounds are used separately (see, e.g., Example 6). In a preferred embodiment of the subject invention, the cells are contacted before, during, and after transfection with one or more compounds from Group I, and are contacted following the transfection step with a compound of Group II, i.e., a sulfonated polysaccharide.

The following parameters have been defined to facilitate and characterize chemical compounds that are useful as agents for prolonging the duration of transient expression. These parameters are called the "X" factor, the "G" factor, and the "K" factor.

$$X = 100 - \frac{(A \times 100))}{C},$$

where "A" is the amount of protein expressed in the control transfected cells during the chosen time period, and "C" is the amount of protein made in cells to which the chemical compound has been added.

This factor reflects the extent to which a chemical compound added to a transfected cell enhances stabilizes transient expression for the first four days following transfection. For chemical compounds active in stabilizing transient expression, the value for X will be >1. For example, if expression is doubled in the presence of a compound, X=50. Preferred compounds will have X>10, and most preferred compounds will have X>25. This factor provides a way of comparing the amount of foreign gene expression observed when a chemical compound of the present invention is present in the culture medium for the first four days after transfection, as compared with the amount of expression observed in control cultures lacking the compound. Thus, the X factor is related to the ratio between the amount of expression observed in the presence and absence of the compound. X may be calculated similarly when the agent in question is a mixture of more than one chemical compound.

Cumulative protein expression, i.e., the values for "A" and "C", is measured by summing the values measured daily in aliquots of the cultured cells. 2. G factors. G factors differ from the X factor only with respect to the time period evaluated. For calculating a G factor, the amount of protein expressed is measured from days 4–7 or days 4–14, where day 0 is the day on which the foreign DNA is added to the cells. The subscripts denote which of the two time periods provided the basis for measurement. Thus, "$G_7$" indicates that the measurements were made between days 4–7, and "$G_{14}$" indicates that measurements were made between days 4–14. As for the X factor, $$G_7 \text{ or } G_{14} = 100 - \frac{A \times 100}{C},$$

where "A" and "C" are defined as for the X factor.

It is useful to characterize compounds according to both the X and G factors, because some compounds having low or negative values for X may have high or positive values for the G factors. Compounds with high values for $G_7$ or $G_{14}$ are especially useful for transient expression where one or more compounds are added to the cultures after the DNA has already entered the cells, i.e., during the second phase of transient expression. Preferred compounds have values for G>0. More preferably G>10, and most preferably, G>25.

3. K factor. The K factor is the ratio of the rate constants for the change in the foreign DNA expression in control transfected cells and in cells exposed to a chemical compound of the subject invention. K is determined according to the following equation:

$$K = \frac{k_{(DNA)control}}{k_{(DNA)compound}}$$

wherein "$k_{(DNA)}$" is the first order rate constant for the change in concentration of the protein expressed from the transgenic DNA, which is expressing protein as a function of time, i.e., $$\frac{-d(DNA)}{dt} = k_{(DNA)},$$

which is equivalent to:

$$\log_{(DNA)} = -\frac{kt}{2.303} + \log_{(DNA)0}.$$

For convenience, the term "d(DNA)" is used here as if it reflected changes in the effective concentration of transfected DNA, though it remains possible that the observed changes in the amounts of foreign gene product depend on parameters other than simply the concentration of foreign DNA in the cells. Hence, the first order reaction rate in control transfected cultures is expressed either as $-k_{(DNA)}$=d(DNA)/dt, or as $\log_{(DNA)}=-kt/2.303+\log_{(DNA)0}$. Thus, when $\log_{(DNA)}$ is plotted against time, the Y intercept, or $\log_{(DNA)0}$, reflects the initial concentration of transfected DNA being expressed. Moreover, the slope of this line while expression is decreasing equals $-k_{(DNA)}/2.303$.

Values for $k_{(DNA)}$ are derived by using a computer program that plots the log of the foreign protein concentration against time, using the results of transgenic protein measurements that begin about 24 hours after the foreign DNA has been added to the cell. Because of sampling error and variability due to a variety of factors, the data points do not usually form a smooth line. However, the program calculates a "best fit" line for each data set, and determines the slope of that portion of the resulting line that corresponds to the period during which protein production is changing. Typically, the largest amounts of protein synthesis are observed during the 48-hour period following transfection. Thereafter, the rate of expression typically declines at a rate that is subject to manipulation by contacting the cells before, during, and/or after transfection with the various chemical compounds of the invention. Thus, the slope is calculated during this period of decline to provide values for $k_{(DNA)}$ and K that can be compared for the purpose of comparing the efficacy of different chemical compounds. For especially effective formulations of the subject chemical compounds, the initial decline in rate of expression is followed by an increase in the rate, or in some cases, no decline is observed throughout the test period.

The K factor thus reflects the effects of chemical compounds on the stability of the foreign gene expression after the foreign DNA is already inside the cell, and not the effects of these compounds on initial DNA uptake. The K factor is important because the advantages of this invention, in contrast with other reported methods for improving transient expression, derive primarily from providing a means for stabilizing transient expression after the transfection step, rather than from the traditional approach of trying to improve the efficiency of DNA uptake. However, some of the chemical compounds of the subject invention have their maximal effectiveness during the first 4 days post-transfection, thus suggesting that they may act by inducing cells to take up increased amounts of the transfected DNA. Such compounds may act as well to prolong the effective half-life of gene expression once the foreign DNA is inside the cell.

Values for K may be positive or negative, which can be understood as follows. K itself is a ratio that compares the rate of change in transgene expression between a test and a control culture. A test culture is one in which a compound of the subject invention is used to enhance transient expression. For control cultures, the amount of transgene expression inevitably declines during the period of comparison, which begins after the transfection step, i.e., usually about 24 hours after adding foreign DNA to the cells. Thus, the slope of the line representing the change in transgene expression for a control culture invariably has a negative value, i.e., a negative slope. For most of the subject compounds, the amount of transgene expression also will decline during this comparison period, though not as much as for the control cultures. Thus, for these compounds, the slope of the line representing change in expression will be negative. In calculating K for such compounds, one in practice divides a negative value derived from the control culture with a negative value derived from the test culture, and obtains a positive value for K. However, some of the subject compounds are so effective that the amount of foreign protein being expressed actually increases rather than decreases during the measurement period. In such instances, the slope of a line plotting this change for the test culture will have a positive value rather than a negative one, and K itself will consequently have a negative value.

Thus, for compounds for which K has a positive value, the absolute value for K will increase with increasing effectiveness of the compound. For preferred compounds for which K is positive, K is preferably greater than 1, and more preferably, K>10, and most preferably, K>50. When the value of K is negative, the absolute value of K will instead decrease with the increasing effectiveness of the compound. Thus, for preferred compounds for which K is negative, K<−1000 to −100, and more preferably K<−100 to −10, and most preferably, K<−10 to −0.001.

In the absence of the chemical compounds of the invention, the decay of transgenic DNA expression, i.e., $k_{(DNA)}$, is a first order reaction. When the chemical compounds of the invention are added to the cultures, the kinetics for transgene expression change dramatically, as compared with control cultures. In the presence of the compounds, $k_{(DNA)}$ becomes increasingly more positive as the production of foreign protein is extended for long periods of time. Indeed, the changes are so dramatic for some of the most preferred formulations, i.e., those in which K>40, that conventional first order kinetics cannot adequately represent the results. Thus, it appears that the preferred compounds/formulations change the kinetics to either a pseudo-first order or a second order reaction, a result not predicted by conventional wisdom.

Many compounds and formulations useful in the subject methods are discussed in the Examples and are included among those listed in these Tables 1, 8, 9, and 10, in which values for X, G, and K are presented.

This invention further provides a method based on the SW480 cell line for screening chemical agents to determine whether they are capable of stabilizing transient expression. Candidate chemical compounds for screening are biocompatible and contain at least one hydrophobic moiety and at least one acidic moiety. The test compound or group of compounds is introduced into a culture of cells, such as SW480 cells, before, during, and/or after the introduction on day zero of foreign DNA that encodes a protein capable of being detected if it is expressed in the cells. As discussed above, a variety of other cell types may be used. To monitor transgene expression following the transfection step, samples of the culture are harvested at regular intervals, e.g., daily, and the amounts of foreign protein in the samples is determined. The amount of protein expressed cumulatively in the culture is determined by summing the amounts measured in the daily samples, and these sums are compared between test cultures, i.e., those that are contacted with the test compound, and parallel control cultures that are not contacted with the compound. Aliquots for protein measurement may be harvested daily between days 0 and 4, or between days 4 and 7, or between days 4 and 14, and the amounts of protein measured are used to determine, respectively, a value for X, $G_7$, or $G_{14}$ according to the formulae given above. If the value thus determined for X or $G_7$ or $G_{14}>0$, it is concluded that the agent enhances transient expression. Preferably, for such compounds X, $G_7$ or $G_{14}>10$, and most preferably, are >25. Chemical compounds so identified may be used to enhance the transient expression of foreign genes in the procedures described above. Preferred product formulations are selected from among those non-toxic compounds and combinations of compounds that exhibit the highest (or most positive) values for the X or G, and that express the most favorable K factors.

Furthermore, the various chemical compounds of the invention can be used together to maximize the enhancement of transgene expression. For example, the various compounds can be used to treat the same culture at different times during the procedure. Different formulations require different combinations of properties. Two distinct types of preferred formulations are:

Type A Formulations: These are compounds having a high value for X. These compounds are highly active immediately following the transfection step, and thus may act during the first phase of transient expression by enhancing the efficiency of DNA uptake. Therefore, the $\log_{(DNA)0}$, or Y intercept, from a semi-log plot as described above, is higher in the case of a Type A compound or formulation than for a control culture, i.e., a culture without these compounds. Such compounds are assumed to affect the efficiency of DNA uptake because the Y intercept is a rough measure of the concentration of active foreign DNA inside the cell immediately following its introduction to the cell. Many of the compounds tested have positive values for the X factor (e.g., see Table 1). Thus, this invention not only provides chemical compounds for stabilizing transfected DNA, but also provides compounds that appear to enhance initial DNA uptake into the cell. Many of the tested compounds had high values for $G_7$ or $G_{14}$ or high positive values for K as well as high values for X, thus are efficacious during both phases of transient expression (e.g., see Tables 1, 3, 8, and 9).

Type B Formulations: Compounds useful in this category have both a high G and K factor. A high value for X also is desirable, but is not required. The most highly preferred Type B stabilizers have values for $G_7$ or $G_{14}>25$, and when K is positive, have a value for K>1, or more preferably, K>10. Furthermore, replicate experiments exhibiting X and/or G factors >25 are required before a particular agent is considered a highly preferred compound in either a Type A or Type B formulation.

For both in vitro and in vivo applications, transient expression is best maximized by the use of both Type A and Type B formulations. For example, a preferred method involves first priming the cells by exposing them prior to transfection to one or more Type A compounds that have a value of X>25. The Type A compounds are also present during transfection, and optimally remain present throughout the period of transient expression. After the transfection step, the cells are contacted for the remainder of the period of transient expression with one or more Type B compounds each of which preferably has a value for $G_7$ or $G_{14}>25$. In a preferred embodiment, the Type A compound is benzoate buffer, and the Type B compound is chondroitin sulfate. Preferably, the chondroitin sulfate has a molecular mass of 20 kDa or less, or more preferably, 9 kDa or less, or even more preferably, 4 kDa or less. In one of the preferred embodiments, the Type A compounds are benzoic acid and 4-ethylbenzoic acid, and the Type B compounds are benzoate buffer and chondroitin sulfate. In yet another preferred embodiment, the Type A formulation includes benzoate buffer and glutamic acid, and the Type B compound is chondroitin sulfate. In another preferred embodiment, the Type B formulation is chondroitin sulfate and lipoic acid, which has the following formula:

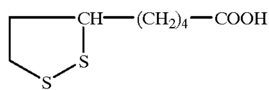

For in vitro applications, the best results are achieved when cells are cultured in the presence of a Type A formulation for several hours, e.g., about 20–24 hours, prior to the transfection step. Priming with a Type A formulation in the form of a dietary (or oral application) is a realistic option in vivo. Many of the compounds effective for enhancing transient infection are known to be non-toxic (see Table 1, below). Cultured cells are optimally maintained in the presence of the Type A formulation for at least 48 hours post-transfection. If desired, the Type A formulation can be removed after about >90% of the cells have taken up the foreign DNA, i.e., several days after the DNA is added to the culture, or this formulation can remain in contact with the cells during the second phase of transient expression. The Type B formulation is optimally added to the cells at the peak of transgene expression, which typically occurs 24–48 hours post-transfection. Optimally, feeding with medium containing a Type B formulation is repeated periodically for the duration of the experiment.

It should be apparent that the subject methods can be used in vivo (i.e., animal studies and clinical procedures). In particular, in the case of gene therapy involving a solid tumor, a Type A formulation may be co-administered with the DNA delivery vehicle, where the recipient tissue is "primed" by injection of a Type A formulation prior to administering the DNA. Thereafter, the Type B formulation is administered.

The useful concentration ranges for individual compounds may vary, and the upper limits of useful ranges may be limited by cytotoxic effects. Direct injection of the DNA/Type A formulation into a tumor would involve only routine procedures, as a variety of pharmaceutical carriers are well-known in the art. Direct injection would avoid exposing non-target tissues to the transfection reagents if this was desired. Choline, liposomal formulations, or controlled release formulations can be combined with a Type B formulation to prolong the localized effect on the transfected tumor cells. In addition, a Type B formulation can be fed to a patient as a dietary supplement (or additive) for extended periods of time after the transgenic DNA has been introduced. Both injection and dietary feeding can be combined for optimal effectiveness according to factors such as toxicity, and the like. This approach offers the advantage of delivering high doses of a cytotoxic protein to a tumor without damaging other body tissues. Using this strategy, the tumor cells themselves would be induced to continuously produce the cytotoxic protein over a period of days, thus providing a far more effective means of delivery than simply injecting a dose of the protein itself into the tumor. This approach is particularly helpful when the protein in question cannot easily cross the plasma membrane if applied externally, or in cases where the protein has a short intracellular half-life.

In other embodiments of the invention, a compound selected from Group I may be linked covalently or non-covalently to a compound selected from Group II, e.g., chondroitin sulfate.

EXAMPLE 1

Screening Assay for Enhancement of Transient Expression

Protocol for control transfections:

The following procedures were used to provide transient expression:

DW480 P3 (ATCC #CCL228) human colon carcinoma cells (typically, $1\times10^6$ cells) were plated in the wells of a 6-well tissue culture plate. The number of wells plated reflected the number of days post-transfection during which the experiment would proceed. Each well contained 1 ml of complete media from a 30 ml stock solution containing 26.4 ml RPMI tissue culture medium, 4 mM L-glutamine, 3.0 ml fetal bovine serum, and 10 $\mu$g/ml gentamicin. Cells were cultured at 37° C. in a $CO_2$ incubator with 10% $CO_2$ for 24 hours after being plated, during which time the cells adhered to the plates.

After the 24 hour pre-incubation step, the transfection step was carried out by removing the RPMI and adding 900 $\mu$L OPTI-MEM® (Gibco) medium containing 2 $\mu$l of VR1412 DNA, (Vical, Inc., San Diego, Calif.), which expresses the bacterial β-galactosidase gene under the control of a cytomegalovirus promoter, and 8 $\mu$g of a mixture of cationic lipid (1,2-dimyristyloxyproply-3-dimethyl-hydroxyethyl ammonium bromide (e.g., "DMRIE/DOPE") mixed in equimolar proportions with dioleoylphosphatidylethanolamine) to yield a lipid:DNA molar ratio of 0.99:1. It should be noted that typical transient transfection protocols employ 10 $\mu$g DNA per $10^6$ cells, but the protocol described here uses less DNA in order to reduce toxicity to the cells. The plates were then incubated for 4 hours at 37° C.

After the 4 hour incubation step, 100 $\mu$l of heat deactivated fetal bovine serum (to stop transfection), plus 12.0 $\mu$l of 50 mg/ml gentamicin were added to each well. Twenty-four hours after the addition of foreign DNA to the wells, all of the cells from one well were trypsinized and counted, then $2\times10^4$ cells from each well were lysed and stored in liquid $N_2$ until being used at a later time to determine β-galactosidase concentration. At that time, each of the unharvested wells received 1 ml of the previously defined OPTI-MEM medium (without L-glutamine added). For the remainder of the experiment, one additional well was harvested at 24 hour intervals, and unharvested wells were fed 1 ml of OPTI-MEM (without L-glutamine, and containing the test compounds) every 48 hours.

Protocol for test compounds:

To test various compounds for their efficacy in enhancing transient expression, the protocol described above for control cultures was modified by incorporating the candidate chemical compound(s) into the culture media. The rest of the procedure remained unaltered with respect to the protocol for the control cultures.

Lysed samples from $2\times10^4$ cells were retained for each β-galactosidase assay, and the remaining cells from each well sacrificed daily. The lysates were frozen and maintained in liquid nitrogen until β-galactosidase assays could be conducted. The thawed sampled were assayed for β-galactosidase using a chlorophenol red-based procedure based on chlorophenol red, wherein the colored product was quanitated at 580 nm using an ultraviolet/visible light spectrophotometer.

The results from this assay for a large number of chemical compounds are presented below in Table 1. Table 1 gives values of X determined in experiments in which cultured SW480 human colon carcinoma cells were cultured and transfected with a bacterial β-galactosidase gene using the methods described in the Examples. In Table 1, the G factors marked with asterisks denote values for $G_7$, while the other G values are for $G_{14}$.

For purposes of comparison, Table 1 includes compounds that tested negative in the assay as well as a large number of compounds that tested positive. The pH values shown in Table 1 were determined in aqueous solutions made by diluting stock solutions prepared in culture media with deionized water. Compounds ranging from about pH3 (glutathione) to pH 10 (adrenaline) were observed to be effective for prolonging the duration of transient expression. The preferred pH range is about pH 4.5–10.5.

For this series of tests, a test result was considered positive if the value calculated for any one of X, G, or K exceeded zero.

TABLE 1

| GROUP I CHEMICAL COMPOUND | mM | pH ($H_2O$) | X Factor | G Factor | K Factor |
|---|---|---|---|---|---|
| '3-[BIS(2HYDROXYETHYL AMINO)]-2-HYDROXYL-'1-PROPANE SULFONIC ACID | 1 | 6.81 | −55 | −10 | |
| 3-AMINO BENZENE SULFONIC ACID | 1 | 3.8 | −19 | 32 | |
| 3-METHYL-L-HISTIDINE | 4 | 7.39 | −15 | 55 | |
| 4-AMINO-BENZOIC ACID | 1 | 7.67 | 52, 52 | 96*, −12 | 1, 1 |
| 4-ETHYLBENZOIC ACID | 1 | 6 | 42, 46 | 43, 63 | 1, 2 |
| 4-BUTYLBENZOIC ACID | 1 | 5.94 | −26 | 65 | 9 |
| 4-PENTYLBENZOIC ACID | 1 | 1 | −96 | −88 | |
| 4-HEXYLBENZOIC ACID | 1 | 6.13 | −68 | −26 | |
| 4-OCTYL BENZOIC ACID | 1 | 7.45 | −2314 | −665 | |
| α-AMINO-n-BUTYRIC ACID | 4 | 7.58 | −.19 | 35 | 1 |
| α-KETOGLUTARIC ACID | 1 | 3.75 | 7.28 | 53 | |
| ADRENALINE | 1 | 10.29 | 49 | 68 | |
| ASPARTIC ACID | 4 | 5.75 | 40, −13 | −45, −17* | |
| β-ALANINE | 4 | 8.38 | 0.2 | 33 | 1 |
| α-ALANINE | 4 | 7.27 | 31 | 35 | |
| BENZOATE/HEPARIN | 2.5, 0.1 | 5.51 | −3 | 22 | |

TABLE 1-continued

| GROUP I CHEMICAL COMPOUND | mM | pH ($H_2O$) | X Factor | G Factor | K Factor |
|---|---|---|---|---|---|
| BENZOATE BUFFER (equimolar benzoic acid/sodium benzoate) | 4 | 4.74 | 29, 17, 3, 2, −16, 30 | 41*, 58, 27, 38, 44, 41* | 2, 2, 1, 1, 1, 3* |
| BENZOIC ACID | 1 | 4.21 | −3.1 | 28 | 1 |
| BENZOIC ACID & 4-ETHYLBENZOIC ACID | 1,1 | 5.82 | 41 | 80 | 2 |
| BES | 1 | 6.64 | 77, 57 | 32, −24 | 1, 1 |
| BUTYRATE BUFFER | 2.5 | 6.12 | −169, −275 | 81*, 69* | −9, 8 |
| CARNOSINE | 4 | 8.32 | −8 | 35 | |
| CITRULLINE | 1 | 7.71 | 39 | 46 | 1 |
| COENZYME B12 | N/A | N/A | −17 | 51 | |
| CREATINE | 4 | 7.54 | 0.34 | 28 | |
| CYSTEINE | 4 | 7.24 | −35 | −50 | |
| DIIODOTYROSINE | 4 | 7.23 | −48 | −8* | |
| ETHYL 4-ACETYLBENZOATE | 1 | 7.59 | 49 | 42 | 1 |
| ETHYL 4-ACETYLBUTYRATE | 1 | 5.98 | 51 | 58 | 1 |
| FOLIC ACID | 1 | 6 | −1.4 | 24 | |
| GLUTAMIC ACID | 1 | 4.2 | −17, 8 | −14*, 31* | 2 |
| GLUTAMIC ACID WITH BENZOATE BUFFER | 1 | 4.91 | 44, 45, 3, 44, 42, 53, 44 | 69, 65, 27, 6 9, 76, 10, 69 * | 1, 1, 1, 2, 6* |
| GLUTARIC ACID | 1 | 3.85 | 22 | −77 | |
| GLUTATHIONE | 2 | 3.58 | 2 | 34 | 1 |
| GLYCINE | 4 | 7.27 | −.34 | 40 | 2 |
| HIPPURIC ACID | 2 | 6.46 | 2 | 33 | 1 |
| HISTIDINE | 4 | 6.75 | 26, −30 | 54*, 6 | 1, 1 |
| HOMOSERINE | 1 | 7.4 | 77 | 39 | |
| ISOLEUCINE | 4 | 6.99 | −119 | 30 | |
| L-ARGININE | 4 | 8.66 | 15, 54 | 11*, 57 | |
| L-GLUTAMINE | 4 | 7.14 | −13 | 23 | |
| L-THREONINE | 4 | 8.14 | 28 | 40 | 1 |
| LEUCINE | 4 | 7.88 | −13 | 32 | |
| L-LYSINE | 4 | 8.34 | −39, 18 | −10, 9* | |
| MELANIN | 0.1 | 3.45 | −155, 0 | −453, −173 | |
| METHYLCOBALAMIN | N/A | N/A | 1 | 25 | |
| METHIONINE | 1 | 7.41 | 2 | 36 | 0 |
| N-(4-AMINOBENZYL)-L-GLUTAMIC DIETHYLESTER | 1 | 6.44 | −35 | 8 | |
| N-CARBAMYL-DL-ASPARTIC ACID | 4 | 4.19 | 26 | 115 | |
| N-FORMYL-L-METHIONINE | 1 | 4.34 | 26 | 63 | |
| NICOTINIC ACID | 1 | 6.91 | 12 | 87 | 1 |
| ORNTHINE | 1 | 7.37 | 16 | 28 | |
| PHENYLALANINE | 4 | 6.97 | −12 | 53 | 3 |
| PROLINE | 4 | 7.71 | −22 | 21 | |
| S-CARBAMYL-L-CYSTEINE | 1 | 6.52 | −76 | −74 | |
| SERINE | 1 | 7.4 | 43 | 104 | 1 |
| SODIUM BENZOATE | 1 | 8.14 | −15 | −6 | 1 |
| TAURINE | 4 | 7.88 | −20 | 34 | 2 |
| TRYPTOPHAN | 4 | 6.25 | 55 | 67 | 2 |
| TYROSINE | 4 | 7.88 | 36 | 52 | 2 |
| VALINE | 4 | 8.12 | −18 | 40 | 2 |

Note that those compounds in Table 1 for which X>1 are compounds that increase the degree of transient expression during the first few days post-transfection. Such compounds may influence cells to take up larger amounts of DNA per cell than they otherwise would, or alternatively, may cause a higher proportion of transfected cells to express the foreign DNA than otherwise would have expressed it. It remains possible also that these compounds enhance early transcription or expression. These compounds have not been previously reported to have this effect on transfection. Interestingly, melanin was noted to significantly suppress transient expression.

In addition to those compounds listed in Table 1, additional compounds that have been tested and found capable of prolonging transient expression include t-butyl benzoic acid, ethyoxy benzoic acid, iso-propyl benzoic acid, emthoxy benzoic acid, isobutyl benzoic acid, chondroitin sulfate, and guarans, particularly hydroxypropyl guaran.

EXAMPLE 2

Chemical Compounds Enhance Transient Expression and Reduce Glucose Consumption Additional experiments were performed to further characterize the enhanced transient expression method. For these experiments, the five culture conditions described in Table 2 were tested using the transient expression protocol described in Example 1. Six-well plates were used, and a sufficient number of wells were seeded with SW480 cells so that the cells from individual wells could be harvested as described below. Type A chondroitin sulfate having an average molecular mass of 4 kDa was used for these experiments (Biorelease Corp., Manchester, N.H., No. 409-4k).

TABLE 2

| Plate # | Chemical Compounds | Concentration | Media Type |
|---|---|---|---|
| 1A | Control with gentamicin | — | see above |
| 1B | Control with no gentamicin | see above | see above |
| 2 | Benzoate buffer | 2.5 mM | Pre-transfection |
| | L-glutamine | 4 mM | Transfection |
| | | | Post-transfection feeding |
| 3 | Chondroitin sulfate | 0.1 mM | Pre-transfection |
| | Benzoate buffer | 2.5 mM | Transfection |
| | L-glutamine | 4 mM | Post-transfection Feeding |
| 4 | Glutamic acid | 4 mM | Pre-transfection |
| | Benzoate buffer | 2.5 mM | Transfection |
| | L-glutamine | 4 mM | Post-transfection Feeding |

Each day, one well was harvested for counting, and $2\times10^4$ cells from each harvested well were lysed, and the lysates retained for a β-galactosidase assay. Supernatants from these same wells were retained frozen and used later for evaluation of pH, glucose consumption, and the production of lactate and ammonia. As seen in Table 3 below, the various combinations of chemical compounds used in plates 2, 3, and 4 differed in their ability to enhance and sustain gene expression. Plate 4 had the best overall performance in this experiment, with high X and G factors, Plate 3, the only plate in this experiment that included a Group II compound, clearly showed signs of reduced transfection efficiency (i.e., a low X factor) but showed promise for sustained expression (i.e., a relatively high G factor).

TABLE 3

| | Plate Number | | | | |
|---|---|---|---|---|---|
| Parameter | 1A gentamicin | 1B no gentamicin | 2 | 3 | 4 |
| X factor | n/a | 9 | 30 | −26 | 44 |
| G factor | n/a | 32 | 41 | 51 | 69 |
| Time elapsed | | % X-gal (blue) | | | |
| 24 hr | 60–70 | 85–90 | 80–90 | 85–95 | 95–100 |
| 48 hr | 40–50 | 60 | 50–60 | 70 | 80 |
| 72 hr | 40–50 | 60 | 60–70 | 60 | 70–75 |
| 96 hr | 10–20 | 30 | 50–60 | 55–60 | 30 |
| 120 hr | 10–20 | 20–30 | 30–40 | 20–30 | 30 |
| 144 hr | 10–15 | 10–20 | 20 | 25 | 20–30 |
| 168 hr | 10–15 | 2–5 | 10 | 10 | 2–5 |

Cell culture experiments typically show a standard deviation in the range of 20%. In fact, it is known in the art that transfection efficiency normally varies even among culture dishes within the same experiment (e.g., see Simoni and Gromoll, *J. Endocrinol. Invest.,* 19:359–364 (1996)), hence the variability observed here is not surprising. Accordingly, X and G factors less than 25 were not considered to be significant improvements over the control.

It is notable that the presence of chondroitin sulfate, a polyanionic carbohydrate, allowed the transfection to proceed unimpeded, and it also resulted in a substantial improvement in gene expression. It was observed in other experiments that polyanionic carbohydrates had a tendency to block the transfection process if contacted with the cells before or during the transfection step. Polymers that exhibited this blocking effect when used before or during transfection included dermatan sulfate, heparan sulfate, heparin (see Example 4), carboxymethylcellulose, and N-carboxymethylchitosan N,S-sulfate. However, when added after rather than during the transfection step, heparin was effective in enhancing transient expression; the other polyanionic carbohydrates are likewise expected to enhance transient expression if added in the molecular weight range of about 4 kDa after transfection.

A control experiment (plates 1A and 1B, Table 3) was included in the above-described experimental scheme to determine whether gentamicin, an antibiotic present in the culture media, may have influenced the outcome of the experiments described above. From comparing the results for control plates #s 1A and 1B, it is evident that gentamicin somewhat suppressed protein production. This is suggested by the slightly lower values for X and G factors in controls with gentamicin, i.e., plate 1A, as compared with plate 1B, the control without gentamicin. Furthermore, results from the β-galactosidase assays supported this conclusion.

Glucose consumption and lactate production, as well as ammonia production, in these same cell samples were analyzed. Glucose and lactate were measured using a Kodak Ektachem DT60 II Analyzer according to standard protocols provided by Kodak and routinely used for measuring serum glucose and lactate levels in clinical laboratories. The analyses are conducted by applying 10 μl of each test sample to a well on a plastic slide covered with a film containing all the regents necessary for measuring either glucose or lactate (Ektachem DT slide (GLU) or Ektachem DT Slide (LAC)). For measuring glucose, the analysis is based on the glucose oxidase-catalyzed reaction of glucose with molecular oxygen, followed by a second reaction that produces a red dye whose intensity is proportional to the amount of glucose in the sample. The slide for measuring lactate similarly provides enzymes and substrates capable of producing a red dye in an amount proportional to the amount of lactate applied to the slide. Slides are placed in the Ektachem DT60 II Analyzer in which the red color is read by reflectance spectrophotometry. Ammonia analysis was performed similarly, using Ektachem DT slides ($NH_3$), based on a reaction wherein $NH_3$ reacts with bromphenol blue to yield a blue dye detectable with the same instrument.

The results of measuring glucose and lactate concentrations as a function of time are presented in Table 4. Table 4 indicates, surprisingly, that the control with gentamicin (plate 1A) consumed more glucose and produced more lactate than any of the experimental samples, which also contained gentamicin (note that the control without gentamicin, i.e., plate 1B, is not included in Table 4). The data of Table 4 provide a clear indication that relative to the control the cells that received the chemical compounds described in Table 2 experienced a profound shift in metabolism that corresponded with a substantially higher level of expression of the foreign gene.

In addition to the data in Table 4, a combination of benzoic acid and 4-ethylbenzoic acid also have been observed to result in reduced glucose consumption. Here, an experiment was conducted in which a Type A formulation was first applied to SW480 cells before and during the transfection step, and a Type B formulation added one day after the DNA was introduced into the cells. The Type A formulation consisted of OPTI-MEM containing 1 mM benzoic acid, 1 mM 4-ethylbenzoate, and 4 mM L-glutamine, while the Type B formulation contained these same components and in addition contained 0.1 mM chondroitin sulfate. Gentomicin was also present throughout the experiment. In this experiment, essentially no glucose consumption was observed in cells cultured in 6-well plates for as long as 14 days post-transfection, or for as long as 32 days post-transfection in bioreactors, during which time the cells continued to express protein from the transfected DNA.

TABLE 4

| Plate # | Day | Glucose Concentration (mg/dL) | Lactate Concentration (mmol/L) |
|---|---|---|---|
| 1A. | 0 | 218 | 1.5 |
| | 2 | 180 | 6.0 |
| | 4 | 141 | 9.6 |
| | 6 | 38 | >12.0 |
| 2. | 0 | 209 | 1.8 |
| | 2 | 188 | 5.0 |
| | 4 | 175 | 6.5 |
| | 6 | — | — |
| 3. | 0 | 213 | 1.6 |
| | 2 | 195 | 4.3 |
| | 4 | 185 | 6.1 |
| | 6 | — | — |
| 4. | 0 | 209 | 1.6 |
| | 2 | 199 | 3.8 |
| | 4 | 181 | 5.7 |
| | 6 | 140 | 9.5 |

It has been previously reported that butyrate, a Group I compound, when administered to cultured hepatocytes compensates for the effects of glucose-starvation on post-translational glycosylation, most likely increasing the intracellular glucose pool (Morrow et al., *Biochem. Biophys. Res. Comm.* 112:115–125 (1983)). However, Morrow et al. did not assay the consumption of glucose in their cultures, thus did not observe the shift in metabolism that is noted here in the presence of Group I compounds. The observed shift in glucose metabolism is a highly significant feature of this invention. Not only does it correlate with the enhanced efficacy of chemical compounds relevant to gene therapy methods (as is evident from this example), but suggests that the ability to selectively and non-toxically redirect cellular metabolic processes with these same chemical compounds could be applied to a wide range of therapies, including, for example, the modulation of fat/lipid metabolism in treating obesity.

EXAMPLE 3

Enhanced Transient Expression in Bioreactors

A series of four lipofection-based gene transfection experiments were conducted in a high performance hollow fiber perfusion prototype bioreactor device (hereafter referred to as the "HPBr" device) in a Genespan prototype incubator instrument. The device consists essentially of a sterile chamber through which two sets of hollow fibers are passed. Culture medium is continuously circulated through one set of fibers, while gases required (e.g., oxygen and carbon dioxide) for cell growth are passed through the second set of fibers. The fibers are composed of a porous material through which gases and nutrients can pass in one direction, while waste molecules produced by the cells growing within the chamber can pass in the other direction. Cells growing in the device may remain in suspension, or may attach to the outer surfaces of both sets of hollow fibers.

A useful feature of the HPBr device is that the cells can be agitated by rotating the chamber through which the tubes pass. When the chamber is rotated 120° in one direction around its longitudinal axis, then 120° in the other direction, this constitutes one "cycle" of rotation. Alternatively, cultures can be grown under "static" conditions, using no rotation.

The HPBr device was used to conduct a series of experiments using SW480 cells. Each experiment included a parallel control in which the cells were plated in a conventional 6-well plate that was placed in a conventional 10% $CO_2$ incubator. The control 6-well plates were cultured and transfected using the protocol described above for the control plates in Example 1, while the following experimental procedures were employed for the bioreactor devices.

HPBr Device Experiments

Four β-galactosidase reporter gene transfection experiments were conducted in HPBr devices using a protocol similar to that described in Example 1 for 6-well plates, although volumes of the various reagents had to be adjusted proportionately to accommodate the larger volumes and higher number of cells in the bioreactors. Due to the perfusion mode of cell culture which is characteristic of the HPBr (i.e., continuous feeding), there was no requirement for periodic feeding by hand.

Procedures for the bioreactor experiments differed in the following ways from the procedures described in Example 1. Sufficient Cytodex®[1] microcarriers (i.e., microspheres composed of crosslinked dextran with positively charged quarternary ammonium functional groups on the surface for cell attachment; Sigma, St. Louis, Mo.) were pre-swollen in phosphate-buffered saline and introduced into the side ports of the HPBr. Approximately 1 microcarrier bead per 10 cells were used. At the onset of the experiment, $1\times10^7$ viable SW480 cells and $1\times10^6$ beads were co-injected into the device. The media described in Table 5 were present when the cells were seeded into the device. Table 5 identifies the rotational parameter ("cpm," corresponding to cycles per minute) employed in this study. A volume of 839 ml of medium were added to each bioreactor. Chondroitin sulfate (Biorelease No. 409-4k) at 0.1 mM was included in the OPTI-MEM transfection media for runs 2, 3, and 4 ("runs" refer to separate experiments). Following the transfection step, the recirculating OPTI-MEM medium (i.e., the medium inside the tubes) was replaced, but the medium in the compartment containing the cells (the extracapillary space) was not replaced. The replacement medium included the compounds listed in Table 5. Liposomes containing the foreign DNA were added to the extracapillary space 24 hours after the cells were seeded into the bioreactors. This space has a small volume (17 ml) as compared with the volume inside the tubes (839 ml).

TABLE 5

| RUN | TYPE | CONDITION | MEDIA COMPOSITION |
|---|---|---|---|
| 1. | Plate | $CO_2$ Incubator [control] | OPTI-MEM (see Example 1) |
| 2 | HPBr | 30 cpm | OPTI-MEM; 10% fetal bovine serum; 4 mM L-glutamine; 10 g/ml gentamicin; 2.5 mM benzoate buffer; 0.1 mM chondroitin sulfate [also present in OPTI-MEM transfection media]. |
| 3. | HPBr | Static | Same as run #2. |
| 4. | HPBr | 30 cpm for first 48 hr., then static | Same as run #2. |
| 5. | HPBr | Static [control] | OPTI-MEM |

Daily samples (about 1.5 ml) of cells and supernatant were taken from the cell compartment of each bioreactor and an equal volume of fresh media was added to replace it. Cell counts and viabilities were determined, and $2\times10^4$ viable cells were lysed and retained for β-galactosidase determination using the spectrophotometric method described in Example 1.

Table 6 contains data comparing the results from four perfusion device experiments (runs #2–5) with a plate control (run #1). In Table 6, the column labeled "area under the curve" refers to the area under a curve in which the amount of β-galactosidase produced in the daily aliquots of harvested cells were plotted as a function of time for the two-week duration of this experiment. Thus, the values in the "area under the curve" column thus are expressed in arbitrary units, i.e., $cm^2$, and reflect the total amount of β-galactosidase produced on a per cell basis for the duration of the experiment. The last column in Table 6 shows for each run, i.e., each plate or bioreactor, the sum amount of β-galactosidase present at day 13 in all of the viable cells remaining at that time.

It is evident that the perfusion bioreactor can be employed to scale-up gene transfection and harvesting transfected cells, which is advantageous for therapeutic application (e.g., for creating large numbers of T-lymphocytes and hematopoietic stem cells expressing foreign genes either stably or transiently, e.g., to be used in somatic cell therapy). This system can also be utilized as an artificial organ so that the long-term expression of the foreign gene can be easily and realistically studied; in a way, this is equivalent to taking a biopsy from an intact organ in vivo.

β-galactosidase are expected to be effective for other proteins as well, and similar experiments will be conduced to evaluate the effects of delivering various proteins, e.g., DNA encoding therapeutic proteins, directly into solid cell masses in vivo.

The bioreactor system used with the methods of the subject invention is useful for creating large numbers of cells genetically modified to express a foreign protein. Such cells can be administered to patients for therapeutic purposes and maintained thereafter in an active state only for as long as the therapeutic regimen dictates. Thus, the subject invention provides a unique form of gene therapy wherein the introduced gene can be turned off simply by restricting its access to the stabilizing substances, i.e., by administering cells transiently expressing a therapeutic protein, then administering the enhancing compounds for only so long as continued transgene expression is desired.

Finally, it should be noted that the use of chondroitin sulfate is important as it enabled the anchorage-dependent cells to adhere well to the microcarrier despite the relatively high rotational speed. This results indicates the compounds of Group II when added to the culture medium are useful for providing anchorage to solid substrata for cultured cells.

TABLE 6

2-Week β-Galactosidase Production in Plate and HPBr Device

| Run | Experimental Conditions | Total # Cells (13 Days) | % Viability | Area Under Curve ($cm^2$) | β-Galactosidase Expression per $2 \times 10^4$ Cells as % of Control | ng/ml β-Gal per $2 \times 10^4$ Cells at Day 13 | Total Expression Based on Viable Cells at Day 13 |
|---|---|---|---|---|---|---|---|
| 1 | Plate Control | $6.5 \times 10^6$ | 97% | 70 | — | 0.084 | 33 |
| 2 | 30 cpm | $1 \times 10^7$ | 86% | 84 | 20% | 0.120 | 65 |
| 3 | Static | $2.3 \times 10^7$ | 42% | 105 | 50% | 0.602 | 364 |
| 4 | 30 cpm/48 hr then static | $7.3 \times 10^7$ | 77% | 180 | 157% | 0.357 | 1254 |
| 5 | Bioreactor Control (Static) | $29.3 \times 10^7$ | 34% | 76 | 9% | 0.040 | 249 |

The data in Table 6 show that manipulating the rotational parameter of the bioreactor provides a unique and convenient means for enhancing transfection efficiency and sustained transient expression in using this device.

As discussed above, microspheres can be introduced into the chamber in order to provide attachment sites for cells. It has been observed, for example, that when an immortal mouse melanoma cell (i.e., ATCC #B16-F0) is introduced into the chamber with microspheres present, the microspheres act as "seeds" for the accumulation of large masses of cells. It was further observed that these masses of cells could be transfected and that thereafter the cells in these masses transiently express the transfected DNA. Samples are readily obtainable from such cultures by sampling the medium within the chamber. This sampling is accomplished by directing a flow of fresh media from a syringe against the cell mass, which results in a number of cells sufficient for sampling becoming suspended in the medium. The masses of cells resemble a solid tumor and provide a model system for developing therapeutic methods effective in delivering therapeutic proteins to tumors in vivo.

Using the same protocols that are effective for cell masses growing inside the bioreactor, melanoma cells will be injected subcutaneously into mice, allowed to develop into tumors at the site of injection, and then liposomes containing the β-galactosidase vector DNA will be introduced directly into the tumors to achieve transient expression of the β-galactosidase. The methods effective for expression of

EXAMPLE 4

Assay for Cytotoxicity

A number of chemical compounds were tested in 6-well plates according to the protocol described in Example 1 to determine the relationship between their cytotoxicity and their ability to promote the uptake and expression of foreign genes in SW480 cells. Unless otherwise noted, except for the control, all plates contained 4 mM L-glutamine as well as gentamicin to retard bacterial growth.

Cytotoxicity assays were performed as follows. SW480 cells (approximately $1 \times 10^6$ cells per well) were plated in 1 ml of RPMI in 6-well culture dishes at day zero in the presence of the chemical compound whose cytotoxicity was being tested. Twenty-four hours after seeding the wells, the RPMI medium was removed, and liposomes containing foreign DNA were added to the culture in 1 ml of OPTI-MEM medium, as described in Example 1. The transfection medium also contained the chemical compounds whose cytotoxicity was being tested. Control plates were included that were identical to the test plates, except that the test compounds were not present in the culture medium. Test and control cultures were grown under "static" conditions, i.e., the plates were not shaken, rotated, or otherwise agitated. Each day for a total of 8 days, the cells from one test well and one control well were harvested and viability assessed by staining with trypan blue. In control cultures exposed to lipsomal DNA, the cell number remained fairly constant or increased only slightly for the first 4 days post-transfection, then increased to about $1\times10^7$ per well by the end of 8 days. The retardation of growth of control cultures during the first 4 days was presumably due to the mild cytotoxic effects of the liposomal DNA itself. A compound being tested was considered "cytotoxic" at the test concentration if a >50% decline in the number of viable cells was observed within 4 days after the introduction of foreign DNA, and furthermore, there was no net expansion of the cells at the end of 8 days. The chondroitin sulfate used here was as in Example 2.

By applying this test protocol, it was possible in many cases to manipulate the concentrations of individual compounds or formulations of compounds to arrive at concentrations well-tolerated by SW480 cells yet also capable of enhancing the levels of transient expression in these cells. Other cells types also were tested for their ability to tolerate some of the chemical compounds of the subject invention. For example, human melanoma cells, mouse melanoma cells, and COS-7 cells (ATCC CRL 1651) were tested for their ability to tolerate the formulations applied to plate #6 in Table 9. The cells differed somewhat in their sensitivity to the tested compounds, but a set of concentrations was identified that could be tolerated by all of these cells types, i.e., at these concentrations the compounds were not cytotoxic according to the above-described assay.

Figure 2:
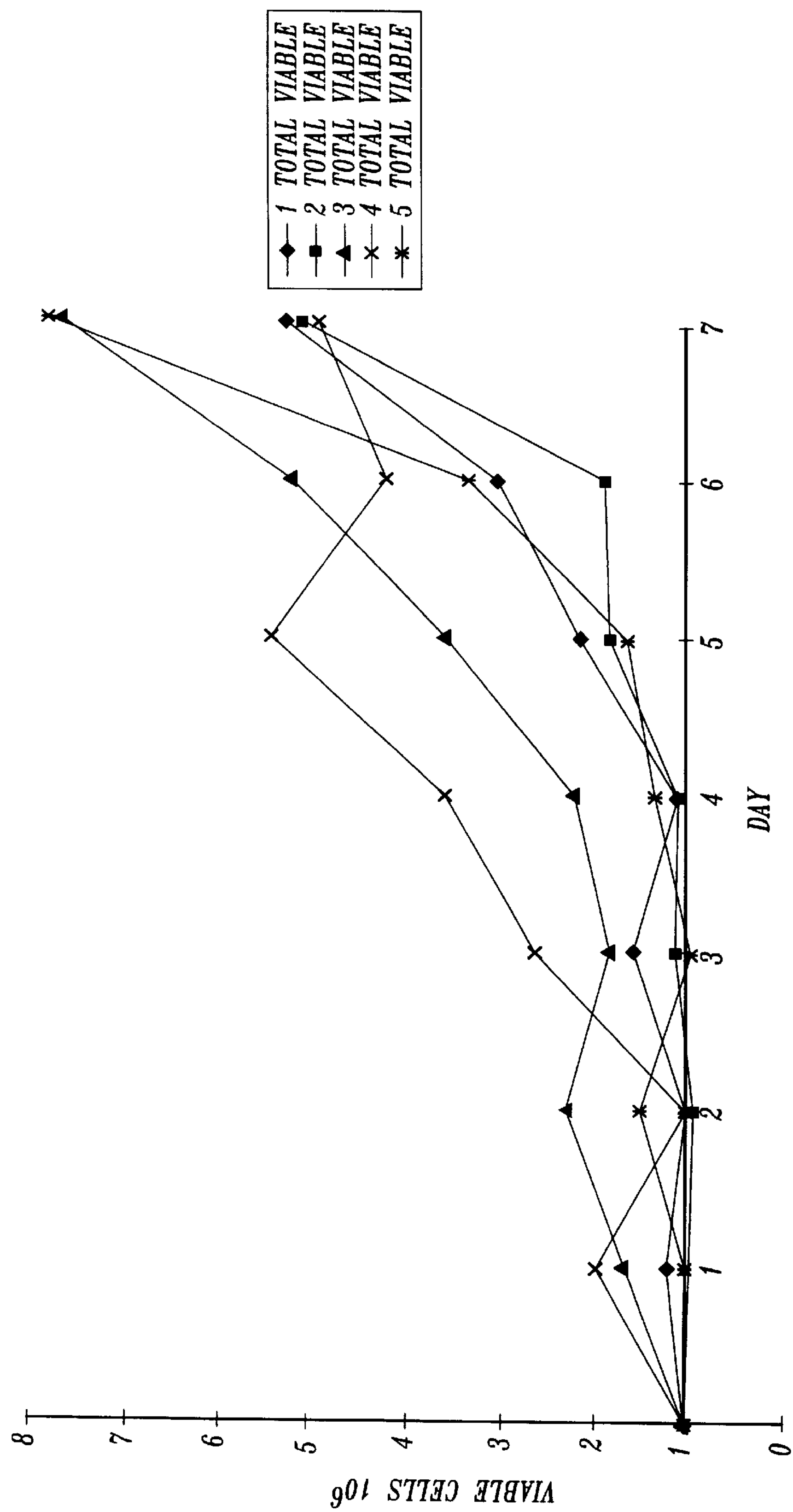
FIG. 2 graphically illustrates the cytoxicity of some of the compounds whose test results are presented in Table 7. The numbers in the inset boxes of FIG. 2 correspond to the plate numbers listed in Table 7.

Sulfonated amino polysaccharides that enhanced transient expression were all found capable of supporting normal cell growth, i.e., they were not too toxic to be tolerated by the cells at concentrations at which they enhanced transient expression. The cell growth and cytotoxicity curves for the cells exposed to the various chemical compounds and formulations in Table 7 are presented in FIGS. 1 and 2, in which the numbers describing each plot correspond to the plate numbers in Table 7. Table 7 illustrates that the polysaccharide heparin (about 6 kDa; Sigma), when present during transfection, blocked transient expression, but that chondroitin sulfate (Biorelease, Type A) enhanced transient expression under these same conditions. The heparin-mediated suppression of gene expression may have resulted from the formation of complexes between heparin and the cationic lipid in the liposomes, thus leaving the DNA without a carrier to deliver it to the cells. However, heparin was observed in other experiments to enhance transient expression when added to the cells after the transfection step. Hydroxypropyl guarans also were observed to enhance transient expression to some degree, though not as effectively as chondroitin sulfate (see Example 10).

TABLE 7

| Plate # | Compound/Formulation | Group | Transgene Expression | Cytotoxic |
|---|---|---|---|---|
| 1 | Control<br>4 mM L-glutamine | n/a | Yes | No |
| 2. | 2.5 mM benzoate buffer<br>0.1 mM chondroitin sulfate<br>4.0 mM L-glutamine | I & II | Yes | No |
| 3. | 2.5 mM benzoate buffer<br>0.1 mM heparin<br>4 mM L-glutamine | I & II | No | No |
| 4. | 0.1 mM heparin<br>4 mM L-glutamine | II | No | No |
| 5. | 0.1 mM chondroitin sulfate<br>4 mM L-glutamine | II | Yes | No |
| 6. | 2.5 mM butyrate buffer | I | Yes | Yes |

TABLE 7-continued

| Plate # | Compound/Formulation | Group | Transgene Expression | Cytotoxic |
|---|---|---|---|---|
| 7. | 2.5 mM butyrate buffer<br>4 mM L-glutamine | I | Yes | Yes |

The plates containing butyrate expressed the transfected gene, however, this buffer was cytotoxic to the SW480 cells under the experimental conditions used for this set of experiments.

EXAMPLE 5

Transfection with Starburst Polymers

This set of experiments addressed the issue of whether the efficacy of the subject methods for enhancing transient expression were dependent on the means by which the DNA is delivered to the cells. Two different combinations of chemical compounds (see Table 8) were employed in transfecting SW480 cells using a protocol similar to that in Example 1, except that here the DNA was introduced into the cells in the presence of polymeric dendrimers instead of using liposomal delivery. These dendrimers are microscopic synthetic polymer spheres (first commercialized by Dow Chemicals as "starburst" polymeric bead standards to be used for sizing), which can be chemically derivatized to play the role of a cationic lipid. The dendrimers employed in this example were provided by F. C. Szoka, Jr., Department of Pharmacy/Pharmaceutical Chemistry, University of California, San Francisco, Calif. While the detailed mechanism of gene delivery for either lipofection or dendrimer-mediated processes is not known, based on physicochemical properties such as their shape and distribution of chemical moieties, they are highly likely to be quite different.

The procedure used deviated from that of Example 1 in the following steps. Fourteen μg DNA were diluted into 397 μl deionized water, and 56 μg of the dendrimer was diluted into 393 μl deionized water. The DNA solution and dendrimer suspension were combined no more than one hour before use. OPTI-MEM medium (733 μl) and the DNA/dendrimer mix (167 μl) were added to each well, and the 6-well plates were swirled by hand to ensure thorough mixing. After incubating for 5 hours, the DNA/dendrimer-containing media was removed and 1.0 ml of culture medium was added. The remaining steps in the procedure were as described in Example 1.

As illustrated in Table 8, the tested compounds were efficacious when dendrimers were used as the method for delivering the foreign DNA to the cells. The chondroitin sulfate used for these experiments was as in Example 2. These findings strongly suggest that the formulation of chemical compounds shown in Table 8 exert their effect after the DNA enters the cell, and thus are effective regardless of the method used to introduce the DNA.

TABLE 8

| Plate # | Compound/Formulation | X Factor | G Factor | K Factor |
|---|---|---|---|---|
| 1. | Control | n/a | n/a | n/a |
| 2. | 2.5 mM benzoate buffer<br>0.1 mM chondroitin sulfate<br>4 mM L-glutamine | 14 | 63 | 2 |

TABLE 8-continued

| Plate # | Compound/Formulation | X Factor | G Factor | K Factor |
|---|---|---|---|---|
| 3. | 2.5 mM benzoate buffer<br>4 mM glutamic acid<br>4 mM L-glutamine | 42 | 34 | −2 |

EXAMPLE 6

Protein Production During Transient Expression

The following experiment illustrates that the subject transient expression system is useful for the rapid production of large amounts of a protein product expressed by a foreign gene that is introduced into recipient cells using the methods described in the preceding examples.

A 15 plate experiment was conducted in which the chemical compounds indicated in Table 9 were added to the culture medium of SW480 cells that were transfected in 6-well plates as detailed in Example 1. The X, $G_{14}$ and K factors, plus the cumulative amount of protein produced in 14 days in $2\times10^4$ cells, were calculated and are shown in the last column of Table 9. The data presented in Table 9 illustrate that all of the listed compositions were superior to the control with respect to the amount of protein produced in their presence. The chondroitin sulfate used for these experiments was as in Example 2. The most efficacious formulations, in order of their effectiveness, were those used in plates 6, 3, 13, and 14. Superior results were observed in the plates that received both Type A and B formulations, thus, these combinations are especially useful for animal testing, e.g., as in treating tumors with toxic proteins, delivering hormones to specific tissues, or other pathological conditions where local delivery of a bioactive protein may be desirable. In other experiments, it was observed that α-lipoic acid could be substituted for benzoate buffer to yield comparable results when used in conjunction with chondroitin sulfate as in plates 6 or 13.

TABLE 9

| Plate # | Compound/Formulation | X Factor | $G_{14}$ Factor | K Factor | Total Protein (ng/ $2\times10^4$ cells) |
|---|---|---|---|---|---|
| 1. | control (DNA but no compounds) | n/a | n/a | n/a | 10.2 |
| 2. | 2.5 mM benzoate buffer | −16 | 43 | 1 | 11.7 |
| 3. | 2.5 mM benzoate buffer<br>Cells fed after 48 hr with Type B Formulation:<br>2.5 mM benzoate buffer<br>0.1 mM chondroitin sulfate | −14 | 63 | 2 | 28.7 |
| 4. | 4 mM tryptophan | 55 | 67 | 2 | 34.2 |
| 5. | 1 mM benzoic acid<br>1 mM 4-ethylbenzoic acid | 41 | 80 | 2 | 27.5 |
| 6. | Type A Formulation<br>1 mM benzoic acid<br>1 mM 4-ethylbenzoic acid<br>Cells fed after 48 hr with Type B Formulation:<br>2.5 mM benzoate buffer<br>0.1 mM chondroitin sulfate | 20 | 82 | 42 | 26.2 |
| 7. | 1 mM 4-ethylbenzoic acid | 47 | 64 | 2 | 21.9 |
| 8. | 1 mM 4-butylbenzoic acid | −26 | 65 | 9 | 14.6 |
| 9. | 4 mM L-glutamine | −12 | 42 | — | 11.7 |
| 10. | 4 mM citrulline | 40 | 46 | 1 | 17.5 |
| 11. | 4 mM benzoate buffer<br>0.1 mM chondroitin sulfate | 54 | 72 | 2 | 26.1 |
| 12. | 2.5 mM benzoate buffer<br>4 mM glutamic acid | 42 | 76 | 6 | 25.1 |
| 13. | Type A Formulation<br>2.5 mM benzoate buffer<br>4 mM glutamic acid<br>Cells fed after 48 hr with Type B Formulation:<br>2.5 mM benzoate buffer<br>0.1 mM chondroitin sulfate | 49 | 78 | — | 28.2 |
| 14. | Type A Formulation:<br>1 mM glutathione<br>1 mM methionine<br>4 mM glycine<br>4 mM α-amino-n-butyric acid<br>1 mM taurine<br>4 mM phenylalanine<br>2.5 mM benzoate buffer<br>4 mM alanine | 57 | 77 | 1 | 29.6 |
| 15. | 1 mM ethyl-4-acetylbutyrate | 51 | 59 | 1 | 22.0 |

Note: Medium in all plates included gentamicin, and except for the control, also contained 4 mM L-glutamine.

These experiments illustrate also the utility of enhanced transient expression for very rapidly producing milligram quantities of protein without the need to first establish cell lines into which the foreign gene has become stably integrated. Thus, enhanced transient expression provides a new means by which candidate biopharmaceuticals can be efficaciously expressed in sufficient quantities to be recovered and rapidly screened for pharmaceutical activity. Thus, the subject invention provides a means for implementing an accelerated drug discovery program. Plate 6, for example, produced about 26 ng β-galactosidase per $2\times10^4$ cells in 14 days (see Table 9). Scaled up to a conventional culture containing around $2\times10^6$ cells, the cumulative protein production using this formulation would be about 2.6 mg. In the HPBr device employed in Example 2, as many as $10^9$ cells are routinely grown, thus in such a culture, tens or even hundreds of milligrams of a novel or interesting protein could be obtained within a matter of a few days.

EXAMPLE 7

Transient Expression in Hepatocytes

A totipotent (stem-cell like) clonal nontransformed cell line (PICM-19 3BT cells; hereafter referred to as "PICM-19 cells") derived from pig embryonic cells epiblast stage), was obtained from Dr. N. Talbots (U.S.D.A., Beltsville, Mass.). These cells behave like hepatic stem cells, showing self-renewing properties for many months when cultured in the presence of 5% or less $CO_2$. At higher levels of $CO_2$, (e.g., up to about 10%), these cells begin to differentiate. At least two different differentiated cell phenotypes have been isolated from differentiated PICM-19 cells, namely, mature hepatocytes and liver ductile cells, which produce bile. PICM-19 cells that had been induced to differentiate were used as a means for determining the transfection characteristics of primary hepatocytes, a cell type that they strongly resemble. In earlier experiments with primary pig liver cultures, results were obtained that mirrored those described above for the SW480 cells. Because the primary liver cultures contained cell types other than hepatocytes, the experiments were repeated with PICM-19 cells providing a homogeneous source of hepatocyte-like cells.

The protocol employed was identical to that described in Example 1 used for transfecting SW480 cells, using $1\times10^7$ cells per well, except that the PICM-19 cells were plated on a layer of mytomicin C-inactivated STO mouse fibroblast feeder cells (CRL 1503), without which PICM-19 cells normally will not grow. In preparing lipisomes, the DNA/lipid to cell ratio was as in Example 1. The incubator was maintained at 10% $CO_2$ throughout these experiments. The PICM-19 cells expanded and under these culture conditions differentiated into mature hepatocytes. To ensure that the differentiation was complete, the cultures were maintained in 10% $CO_2$ for 3 weeks prior to the transfection step.

Table 10 describes the media that were used in a transfection study using these cells, as well as the X, $G_7$ and K factors measured in these cultures. The chondroitin sulfate used in these experiments was as in Example 2. The results shown in Table 10 are consistent with the findings for SW480 cells and the results observed when primary isolates from adult pig liver were transfected under similar conditions.

Figure 3:
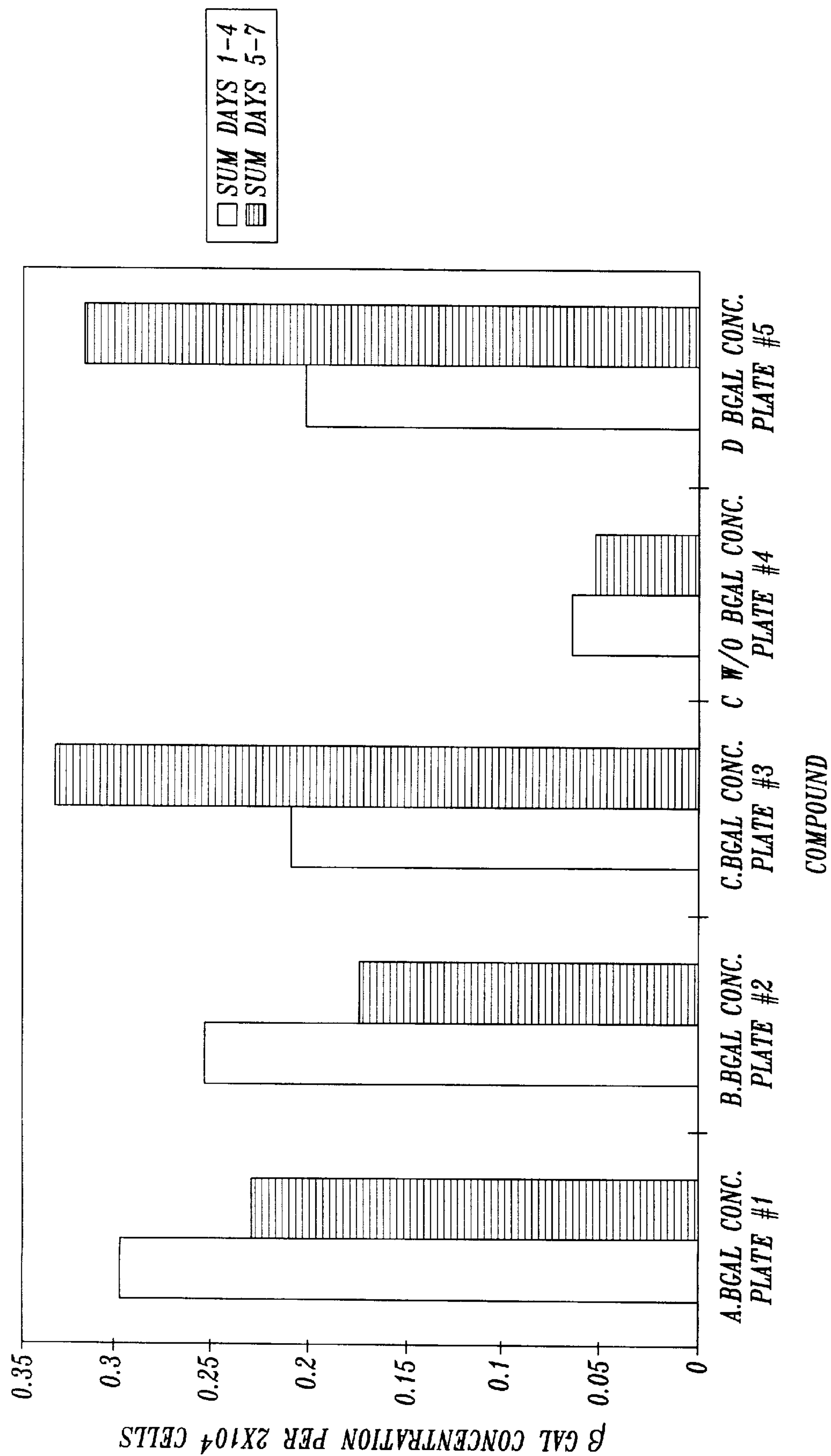
FIG. 3 graphically illustrates the results of the experiments of Example 6. Each pair of bar graphs correspond to one of the plates shown in Table 10, as indicated in the figure. These experiments involved transient expression in differentiated porcine PICM-19 3BT cells, which resemble hepatocytes, in the presence of various chemical compounds that prolong the duration of transient expression.

Surprisingly, it was observed also that the plates lacking feeder cells were capable of supporting differentiated PICM-19 cells for at least 4 weeks. These cells moreover expressed the transfected DNA, as illustrated in FIG. 3, albeit at a reduced efficency as compared with the other test plates. This result was extremely surprising, as there are no reports of hepatocytes being grown or maintained in culture for more than a few days without either a feeder layer or a proteinaceous coating (e.g., collagen) having been applied to the plates' prior to adding the cells. Remarkably, the cells in plate #4 adhered as well as did cells in plates containing feeder cells, suggesting that the chondroitin sulfate created in vivo-like conditions for both cell growth and maintenance. Thus, these experiments demonstrate for the first time the utility of chondroitin sulfate for culturing hepatocytes without feeder cells in a low cost medium composition while maintaining a phenotype similar to that observed for hepatocytes in vivo.

TABLE 10

| Plate # | Compound/Formulation | X Factor | $G_7$ Factor | K Factor |
|---|---|---|---|---|
| 1. | Control | n/a | n/a | n/a |
| 2. | 2.5 mM benzoic acid<br>4 mM L-glutamine | −17 | 99 | 1 |
| 3. | 2.5 mM benzoate buffer<br>0.1 mM chondroitin sulfate<br>4 mM L-glutamine | −41 | 102 | 0.0 |
| 4. | 2.5 mM benzoate buffer<br>0.1 mM chondroitin sulfate<br>4 mM L-glutamine<br>NO FEEDER CELLS | −357 | 103 | 2 |
| 5. | 2.5 mM benzoate buffer<br>4 mM glutamic acid<br>4 mM L-glutamine | −46 | 103 | 0.0 |

EXAMPLE 8

Recovery of Transgenic mRNA and DNA from Transfected Cells Grown in a Bioreactor The high performance bioreactor device (HPBr) described in Example 3 was used in a 32-day experiment in which SW480 cells were transfected and propagated as described in Example 3 and in Table 5. Except as described otherwise below, the conditions and assays used were the same as described in Example 3. At the onset of the experiment, $1\times10^7$ SW480 cells freshly harvested from tissue culture flasks were injected into the HPBr derive concurrently with $1\times10^6$ preswollen microspheres. The cells were then cultured for 24 hours without rotation in medium containing 1 mM benzoic acid and 1 mM 4-ethylbenzoic acid (a Type A formulation). At the end of 24 hours, plasmid DNA encoding β-galactosidase was added, and the bioreactor was rotated at a rate of 30 cpm for 4 hours. The medium containing the DNA was then removed from the extra-capillary space (ECS) of the bioreactor by flushing three times with feeding medium containing 1 mM benzoic acid, 1 mM 4-ethlybenzoic acid, and 0.1 mM chondroitin sulfate (Biorelease Corp., No. 409-4k). This latter combination of reagents is a Type B formulation. Thereafter, the 1 liter bottle of culture medium for circulating through the bioreactor was replaced with a 1 liter bottle of feeding medium containing the same Type B formulation. For the remainder of the experiment, the medium circulating through the bioreactor was replaced every seven days with a fresh 1 liter bottle of feeding medium containing the Type B formulation. The device was not rotated after the DNA was removed so that the cells could form a tumor-like solid mass.

Beginning 24 hours after removing the DNA from the bioreactor, aliquots of cells and culture supernatant from the ECS were removed daily for 32 days. Cell sampling was accomplished by directing a stream of culture medium against the cell mass to dislodge some of the cells, then withdrawing a small volume of the resulting cell suspension. The cells and culture medium in each sample were separated by brief centrifugation. A total of $2\times10^4$ cells from each daily aliquot were analyzed for β-galactosidase and each supernatant was analyzed for its metabolic signature, i.e., its concentrations of glucose, lactate, and ammonia. After collecting the daily sample on day 32, the remaining cells were harvested from the ECS by trypsinization, and $2.8\times10^5$ of the harvested cells were used for the extraction of RNA and DNA.

Figure 4:
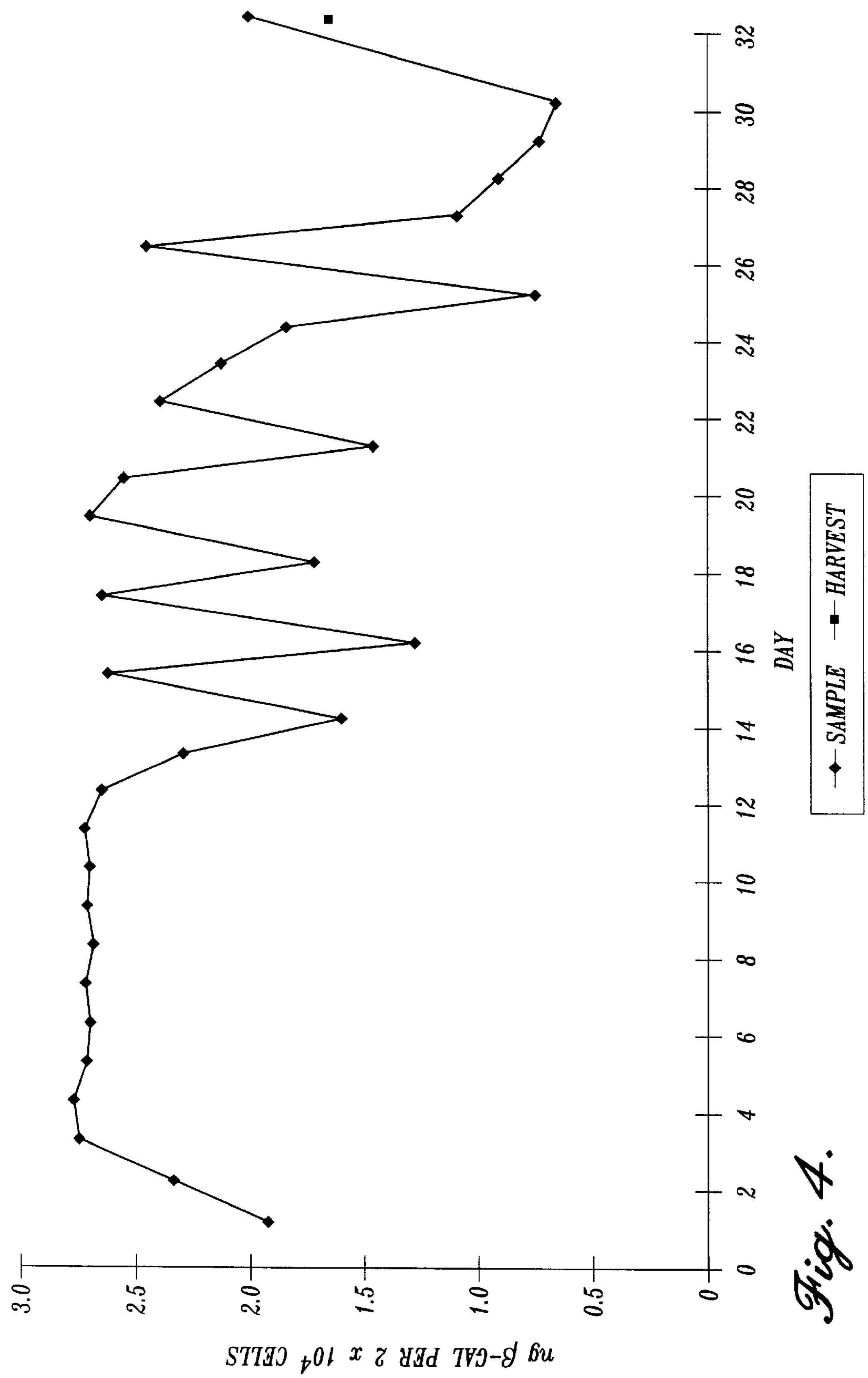
FIG. 4 is a graphic illustration of the amounts of β-galactosidase measured in the samples harvested daily during the experiment described in Example 8, and illustrates the long-term stabilization (i.e., 32 days) of transgene expression in transfected cells cultured in a bioreactor device in the presence of transient expression-stabilizing compounds.

Beta-galactosidase in the daily cell samples was assayed as described in Example 3, and the results of these are illustrated in FIG. 4. FIG. 4 shows that the peak level of expression of β-galactosidase occurred at day 4, and remained virtually unchanged until about day 12, whereafter the values became less consistent but nonetheless remained relatively high. The final data point, corresponding to cells collected by trypsinization at the end of the experiment, is indicated in FIG. 4 by a square-shaped symbol, and its value corresponded to roughly 60% of the peak value. Thus, a relatively high level of β-galactosidase production took place in this culture throughout the entire 32-day period.

Figure 5A:
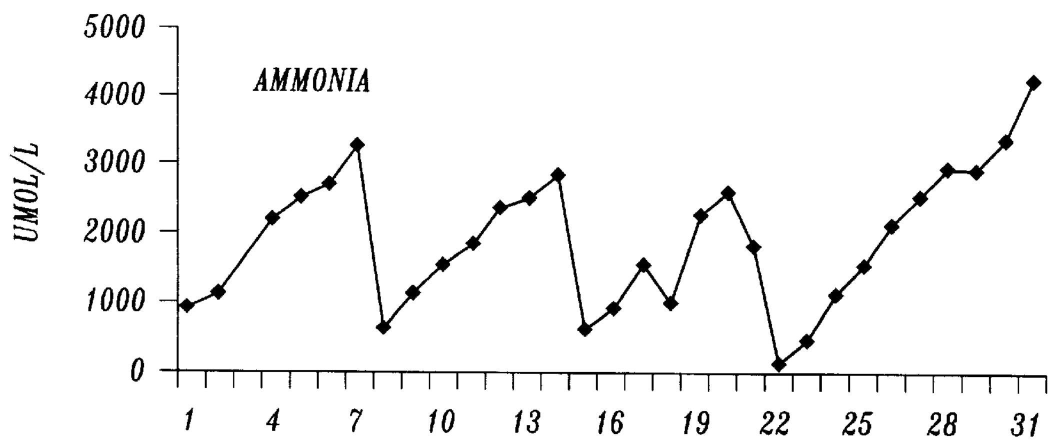
FIGS. 5A–5C graphically illustrate the concentrations of ammonia, glucose, and lactate in the culture medium sampled daily during the experiment described in Example 8.
Figure 5B:
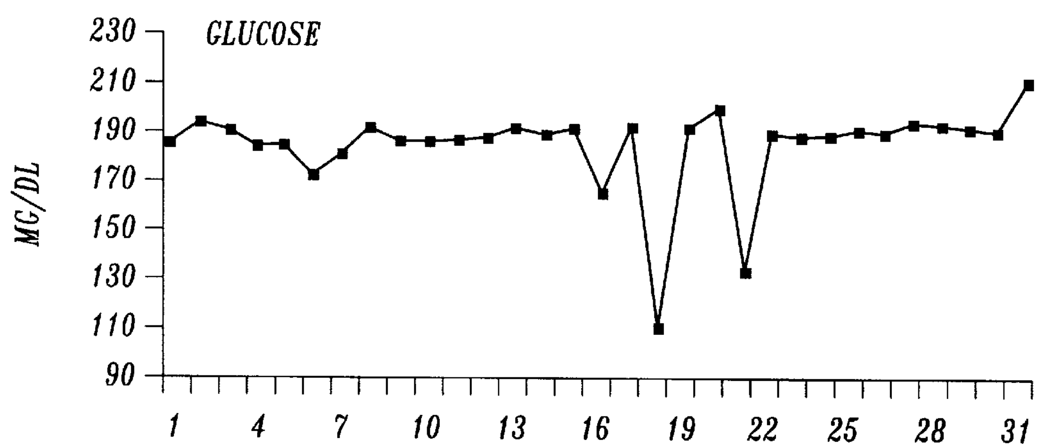
Figure 5C:
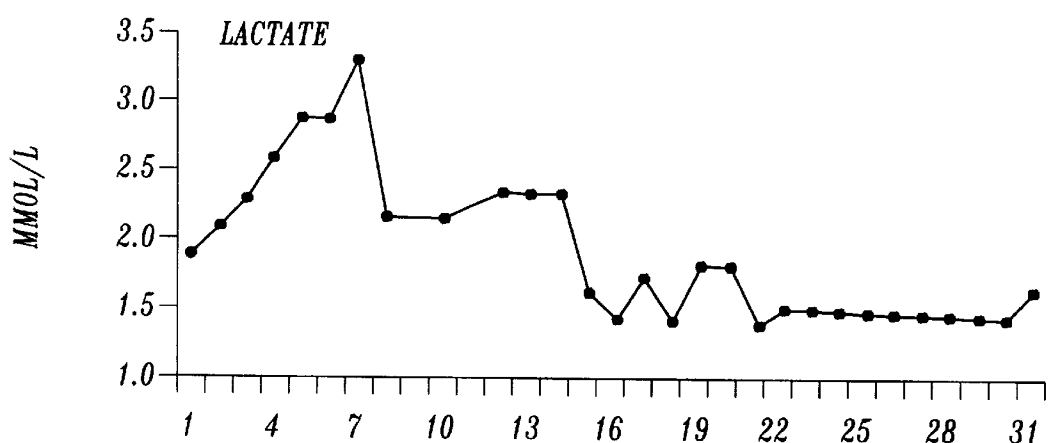

The procedures described in Example 2 were used to measure the concentrations of glucose, lactate, and ammonia in the supernatants, and the results of these measurements are presented in FIGS. 5A–5C. It is apparent from FIGS. 5A and 5B that neither the glucose nor the lactate concentrations changed to a significant extent throughout the course of the experiment (the fluctuations in lactate were not considered significant in view of the low amounts of lactate present in these samples and in view of the relatively constant amounts measured past day 7). In contrast, the ammonia concentration increased over two-fold by the end of each seven-day period between media changes, before dropping back to the base value each time fresh medium was provided. This repeated accumulation of ammonia after each medium change strongly supports the notion that exposure to transfection-stabilizing compounds causes cells to shift their metabolism from using glucose (glycolysis) to using proteins or amino acids instead as their primary carbon source (tricarboxylic acid cycle). Had the cells in this experiment used glucose for their primary source of energy, one would have expected lactate and not ammonia to increase in concentration during each 7-day period (note that FIG. 5B suggests that some glycolysis may have occurred during the first 7-day period).

Ammonia is a byproduct of the deamination that is an early step in the entry of amino acid metabolites into the tricarboxylic acid cycle. Accordingly, the most likely explanation for the accumulation of ammonia in the culture media is that the cells used amino acids, or possibly peptides or proteins, as their source of energy during their exposure to the compounds used to stabilize transient expression. These amino acids may have originated, for example, from peptides present in the culture medium. Such peptides could have been created by the heat-induced breakdown of serum proteins during the heat inactivation of the serum present in the culture medium.

Their ability to cause cells to shift from the use of glucose to the use of amino acids as an energy source has significant implications for the use of transient expression-stabilizing compounds. For example, the tricarboxylic acid cycle by which amino acids are metabolized is critical also in the metabolism of fats and lipids. Thus, treating cells or a human subject with transient expression-inducing compounds may result also in the increased metabolism of fats and lipids by virtue of activating the tricarboxylic acid cycle. Thus, the compounds could serve, for example, as agents for controlling weight. These results also illustrate an association between the unique metabolic signature seen in FIGS. 5A 5C and the physiological state in which the transient expression of transfected genes is enhanced and stabilized.

To prepare nucleic acids, $2.8\times10^5$ trypsinized cells harvested at the end of the 32-day incubation were pelleted by centrifugation, washed with 5 ml of calcium-free and magnesium-free PBS, and mixed with 1 ml of TRIZOL™ (Life Technologies) reagent at room temperature. The cells suspended in TRIZOL™ were then incubated at 4° C. for ten minutes. At this point, the sample was stored frozen at −70° C. After being thawed, the sample was permitted to stand at room temperature for 20 minutes before adding 200 μl of chloroform, mixing vigorously for 15 seconds, and incubating at room temperature for 5–20 minutes. Next, the sample was centrifuged at 2,000×g for 15 minutes at 4° C. to separate the emulsion into two phases.

For isolating RNA, the upper aqueous phase was carefully collected without including any portion of the interphase, and transferred to another tube to precipitate the RNA, 0.5 ml of isopropanol was mixed with this aqueous phase, the tube was incubated at room temperature for 10–20 minutes, and then was centrifuged at 12,000×g at 4° C. to collect the RNA pellet. The pellet was carefully washed with 1 ml of 70% (v/v) ethanol, air-dried for 5–10 minutes at room temperature, and resuspended in 30 μl of RNAse-free water (Five Prime Three Prime).

To isolate the DNA, the lower phase and organic layers described above were collected and mixed by inversion with 300 μl of 100% ethanol, then allowed to stand at room temperature for 2–3 minutes to precipitate the DNA. The DNA pellet was collected by centrifugation at 2,000×g for five minutes at 4° C., then washed twice wit 0.1 M sodium citrate containing 10% ethanol. After the second wash, the DNA pellet was again collected by centrifugation at 2,000 g for five minutes at 4° C., and washed by being resuspended in 75% ethanol for 10–20 minutes at room temperature. The pellet was again collected by centrifugation, briefly dried, and resuspended and dissolved in 8 mM sodium hydroxide.

To detect the presence of β-galactosidase sequences, the concentration of the RNA was determined by reading the absorbency at 260 nm, then the RNA solution was diluted with RNAse-free water to a final concentration of 100 μg/ml. Fifty μl of the diluted RNA solution was then mixed with 150 μl of a 50:50 solution of 37% formaldehyde and 20×SSC. Samples were heated to 55–60° C. for 20 minutes to denature the target nucleic acid, placed on ice, and 200 μl RNA-free water were added. Samples were shaken and briefly centrifuged to pellet debris, then loaded into the wells of a slot-blot apparatus under light vacuum to collect the RNA onto a GeneScreen Plus™ membrane (New England Nuclear). Wells were washed with 50 μl of 10×SSC, and the membrane was exposed to ultraviolet light to crosslink the RNA to the membrane, then was baked for one hour at about 90° C. to remove the formaldehyde. DNA samples were slot-blotted using the same procedure, except no vacuum was used.

The presence of β-galactosidase DNA or mRNA on the slot-blot membranes was determined by hybridization with a $3^2$-P-labeled oligonucleotide corresponding to a portion of the β-galactosidase gene present in the plasmid used for transfection. The nucleotide sequence of this oligonucleotide was 5' CTCCAACGCAGCACCATCAC 3' (SEQ ID NO:1). For hybridization, 10 ml of hybridization buffer (1 ml 50×Denhardt's solution, 10 μl of 10 mg/ml polyadenylic acid, 12.5 ml of 20×SSC, 5 ml of 10% sodium dodecyl sulfate, and 2.5 ml of 0.5 M $NaPO_4$ (pH 6.5) in a final volume of 50 ml) were placed in a plastic bag with the loaded slot-blot membrane and $1\times10^6$ counts/ml of $3^2$P-labeled probe. Bags were sealed and incubated overnight at 52–53° C. After hybridization, the membranes were washed twice with buffer containing 5×SSC and 0.1% sodium dodecyl sulfate for 5–10 minutes at room temperature, then twice more with the same buffer at 52–53° C. for 20–30 minutes per wash, then exposed to x-ray film.

On the resulting autoradiograms, a signal was present indicating the presence of transfected DNA containing the β-galactosidase gene in the cells harvested 32 days after transfection. Thus, the DNA evidently had persisted in relatively high amounts throughout the 32 day test period. Also, the autoradiogram of the RNA slot-blot showed a surprisingly strong signal after hybridization with the β-galactosidase probe. In numerous previous experiments, it was shown that production of β-galactosidase declined and disappeared from cells within 2–3 days after removing the inducing compounds from the culture medium. Thus, it was clear that the observed persistence of detectable β-galactosidase DNA and mRNA in this experiment did not result from the outgrowth of cells in which the foreign DNA had become integrated. Moreover, the typical half-life for an mRNA is only about 1–3 days, thus the presence of β-galactosidase mRNA at the end of the 32-day incubation period suggests that this mRNA was recently transcribed and that the transfected foreign DNA thus must have persisted throughout the 32-day experiment.

The detection of β-galactosidase DNA after 32 days of incubation suggests the possibility that the foreign DNA may have replicated and increased in amount during this period. Because the cells continued to grow and divide during the experiment, one would have expected the plasmid DNA added at day 0 to have become diluted, and therefore that cells analyzed 32 days later would contain very little β-galactosidase DNA. Thus, the surprising presence of easily detectable amounts of β-galactosidase mRNA and DNA suggests that the transfected DNA may have replicated during the experiment, possibly within the mitochondria.

EXAMPLE 9

Induction of Alkaline Phosphatase Enzyme in Cells Treated with Transient-Expression Stabilizing Compounds The results of the following experiment indicated that, in addition to inducing the tricarboxylic acid cycle, the metabolic signature of cells treated as described in Example 8 also includes the induction of an endogenous phosphatase enzyme activity that normally is barely detectable in the culture medium from SW480 cells. Cells were grown in plastic tissue culture dishes, and were transfected and propagated using the same culture media described in Example 8. The cells were fed daily by the addition of a few ml of feeding medium. Aliquots of the culture medium from these plates were harvested daily beginning with the first day post-transfection, and these aliquots were analyzed for concentrations of glucose, lactate, and ammonia as described in Example 8. Unexpectedly, when these same samples were analyzed for endogenous phospatase activity using a standard alkaline phosphatase assay, high amounts of activity were detected. The observed degree of elevation ranged from about 2-fold to about 20-fold, as compared with conventionally-grown SW480 cells.

The assay used was designed to measure "secreted alkaline phosphatase activity" (SEAP) activity as follows. One-half ml of each sample was mixed with 2×SEAP buffer (1×SEAP buffer=1 M diethanolamine, 0.50 mM magnesium chloride, pH 9.8). As a control, bovine intestinal mucosal alkaline phosphatase was assayed concurrently. The bovine alkaline phosphatase was made up in 1×SEAP. The chromogenic substrate for these assays was 0.15 M p-nitrophenylphosphate which yields a product detectable at 405 nm after being cleaved by alkaline phosphatase. The substrate (100 μl) was added to each assay tube, then the tubes were placed at 37° C. Thereafter, the absorbence of the control sample was read each minute for 10 minutes, and that of each test sample at 1 and 6 minutes. The units of phosphatase activity/ml of test sample were determined using the formula:

$$\text{units enzyme/ml} = \frac{\left[\left(\frac{\Delta A\ 405\text{nm}}{\min}\right)\text{sample} - \left(\frac{\Delta A\ 405\text{nm}}{\min}\right)\text{blank}\right] V \times df}{18.5 \times VE,}$$

where:

A405 nm=absorbence at 405 nm,

V=volume in the assay tube, df=dilution factor,

VE=volume of sample added to the assay tube.

For this set of assays, V=1.1 ml, df=2.2, and VE=0.5 ml.

To determine whether the induced phosphatase activity was heat-sensitive, a second set of assays was run on the same samples using assay buffer identical to the SEAP buffer described above, but containing 0.01 M L-homoarginine. The control enzyme samples (Clontech Laboratories) and samples of culture medium were heated in this buffer to 65° C. for 5–10 minutes before adding the substrate. This heat treatment is known to destroy the alkaline phosphatase that is found in most mammalian cells that express the enzyme, and indeed it destroyed the phosphatase activity in these samples, as well as that in the control alkaline phosphatase samples. The pH optimum of the induced phosphatase has not been determined, thus these results do not necessarily establish that the induced phosphatase is an "alkaline phosphatase." Phosphatases commonly found in animal cells includes acid phosphatase, which is found in lysosomes, as well as placental alkaline phosphatase, though other phosphatases may exist.

In numerous experiments, a burst of the induced phosphatase activity was detected in the culture medium at the onset of the period during which the transgenic product begins to disappears from a transfected culture. Thus, a spike in phosphatase activity provides a marker for intracellular events that involve the effective elimination of transgenic DNA from the transfected cell.

EXAMPLE 10

Influence of Molecular Mass on the Effectiveness of Chondroitin Sulfate

The following experiments were conducted to determine the effects of polysaccharide size on their effectiveness in enhancing transient expression. For these experiments, the protocol used was that described in Example 6 for plate #6 (shown in Table 8), except that the compounds described below were substituted for the condroitin sulfate that was added to plate #6/Table 8.

In an effort to assess the degree of variability that can be expected in applying this protocol, the X and $G_{14}$ values were averaged from four separate experiments that utilized chondroitin sulfate with an average molecular mass of 4 kDa. In all four of these experiments, the protocol of plate #6/Table 8 was followed. The chondroitin sulfate used for these comparisons was obtained either from Biorelease, or was prepared by treating large (>20 kDa) chondroitin sulfate (Type A) with alkali, then acid. The size of the non-purchased preparations was determined by electrophoretic comparison with Biorelease 4 kDa chondroitin sulfate using PhastSystem gels in accord with the manufacturer's instruction (Pharmacia). The results are shown in Table 11, in which the ranges observed for X and $G_{14}$ in the four trials are shown in parentheses below the averages. These data indicate that the protocol is fairly reproducible, as similar results were obtained using the two different preparations of chondroitin sulfate. Moreover, with one exception (i.e., the X factor for the 409-4K preparation), a fairly narrow range of variability was observed for the X and G factors. Given that transient expression results typically vary by about 20%, these results indicate an acceptable degree of variability.

TABLE 11

| Chondroitin | Variability: Average Over Four Experiments | | Total β-gal (ng)for |
|---|---|---|---|
| Sulfate | X | $G_{14}$ | 2 × $10^4$ Cells in 14 Days |
| 409-4K (Biorelease) | 36.2 (4.1 – 53.8) | 78.5 (75.1 – 85.0) | 1337.3 (629.1 – 1813.4) |
| Exp-4K | 43.8 (36.8 – 54.5) | 79.7 (74.5 – 85.5) | 1315.0 (795.3 – 1694.1) |

To determine the effects of size on the ability of a polysaccharide to enhance transient expression, chondroitin sulfates of various sizes were tested. This set of trials included both Type A and Type C chondroitin sulfate, as indicated in Table 12. The results of Table 12 clearly show that chondroitin sulfate of >20 kDa is not effective when used in accord with this protocol, but that both 9 kDa and 4 kDa preparations both are effective. Table 12 also presents the results of the Limulus amebocyte lysate (LAL) endotoxin assay, expressed as endotoxin units per ml (Eu/ml), which was performed on all media used before, during and after transfection, but before adding serum. This assay provides a quantitative measure for Gram-negative bacterial endotoxin in aqueous solutions. The LAL assays were performed using the Pyrogent® 03 Plus kit obtained from BioWhittaker, Walkersfield, Md., in accord with the manufacturer's instructions. The LAL results in Table 12 are those for the post-transfection media, assayed prior to adding serum. All solutions used for these experiments were prepared in a hood using standard aseptic procedures.

TABLE 12

| Chondroitin Sulfate | MW (kDa) | Deproteinated (+/−) | FACTOR X | $G_{14}$ | K | LAL (Eu/mL) | Total β-gal (ng) from 2 × $10^4$ cells in 14 days |
|---|---|---|---|---|---|---|---|
| Crude cartilage extract | >20 | − | −466.5 | −183.6 | 0.9 | 0.03 | 135.8 |
| 4D36* (Type A) | >20 | + | −110.3 | −19.6 | 1.0 | 0.06 | 187.5 |
| Type C‡ (Shark) | >20 | − | −466.2 | −148.1 | 1.0 | 0.03 | 108.7 |
| 409* (Type A) | 9 | + | 12.9 | 48.3 | 1.1 | 0.03 | 401.6 |
| Exp-4K (Type A) | 9 | + | −6.1 | 48.2 | 1.9 | <0.015 | 422.7 |
| 4094K* (Type A) | 4 | + | 4.1 | 76.7 | 4.6 | 0.06 | 629.2 |
| Exp-4K (Type A) | 4 | + | 36.8 | 79.9 | −19.2 | 0.015–0.06 | 795.3 |
| Exp-4K (Type C) | 4 | + | 41.7 | 81.0 | 1.19 | <0.015 | 713.3 |

*Biorelease Corp., 340 Granite St., 2nd Fl., Manchester, NH 03102
‡Soft Gel Technologies, Inc., 6982 Bandini Blvd., Los Angeles, CA 90040

Because the results shown in Table 12 suggested that smaller polysaccharide chains yielded better results, additional experiments were performed to determine whether single repeating units derived from chondroitin sulfate would be effective in enhancing transient expression. As shown in Table 13, although the disaccharide units (which are the predominant monomer in the polymer structure) derived from Type C (ΔDi-6S) chondroitin sulfate gave better results than the controls, the disaccharide units (which are the predominant monomer) derived from Type A were determined to be cytoxic, thus unsuitable for use in this procedure. Polymannose, mannose and the 2-hydroxypropyl ether form of guaran also were tested and were found to be effective in enhancing transient expression, as shown in Table 13.

TABLE 13

| Chondroitin Sulfate | Form | FACTOR X | G | K | Total β-gal (ng) from 2 × $10^4$ Cells in 14 Days | Cytotoxic |
|---|---|---|---|---|---|---|
| Exp-4K (Type A) | 4 kDa | 2.2 | 57.1 | 1.1 | 951.7 | No |
| Exp-4K (Type C) | 4 kDa | 27.4 | 75.1 | 1.3 | 1432.1 | No |
| Chondro ΔDi-4S* | single disaccharide unit | −28.2 | 40.1 | 0.4 | 184.7 | Yes |
| Chondro ΔDi-6S* | single disaccharide unit | −32.7 | 39.0 | 1.3 | 932.2 | No |
| Mannose* | mono-saccharide | −23.6 | 23.5 | 1.0 | 730.4 | No |
| Polymannose** (Acemannan) | approx. 4 kDa | 2.7 | 15.7 | 1.0 | 972.7 | No |
| Guran (2-hydroxy-propyl ether)‡ | approx. 4 kDa | −51.8 | 14.4 | 0.8 | 801.8 | No |

*Sigma, #C4045 (ΔDi-45); #C4170 (ΔDi-65)
**Carrington Laboratories, Irving, TX
‡Carbomer, Inc., Westborough, MA In conclusion, it appears that Type C chondroitin sulfate having an average molecular mass of 4 kDa is exceptionally effective in enhancing the production of transgenic protein during the second phase of transient expression.

While the preferred embodiment of the invention has been illustrated and described, it will be appreciated that various changes can be made therein without departing from the spirit and scope of the invention.

What is claimed is:

1. A method of enhancing the transient expression of a foreign gene in a eukaryotic cell in vitro comprising:

introducing into the cell a molecule of foreign DNA that encodes a protein in a form capable of being expressed in the cell;

contacting the cell before, during, or after introducing the DNA with a biocompatible transient expression enhancing agent, provided that said agent is not butyrate or butyric acid;

maintaining the cell in a non-selective medium after introducing the DNA; and, detecting the foreign protein in the cell after maintaining the cell for at least five days to the non-selective medium.

2. The method of claim 1, wherein the transient expression enhancing agent comprises at least one carboxylic acid derivative having the formula:

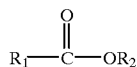

wherein $R_1$ is:

$CHNH_2R_3$, wherein $R_3$ is the side chain of a naturally occurring amino acid;

$C_6H_4R_4$, wherein $R_4$ is H, $CH_3$, $(CH_2)_nCH_3$, $NH_2$, $COCH_3$, $CO(CH_2)_nCH_3$, $C(CH_3)_3$, $CH(CH_3)_2$, $(CH_2)_nCH(CH_3)_2$, $(CH_2)_nCOCH_3$, $OCH_3$, or $O(CH_2)_nCH_3$, wherein n=1–3;

$CHNH_2(CH_2)_nR_5$, wherein n=1–7 and $R_5$ is $CH_3$, OH, $CONH_2$, $C_6H_4OH$, or $CONHNH_2$;

$(CH_2)_nR_6$, wherein n=1–9 and $R_6$ is an indole group, $NCH_3C(=NH)NH_2$, $SCH_3$, $NH_2$, $CH_3$, $CO_2H$, $CONH_2$, or $NHC(=NH)NH_2$, provided that when n=2 and $R_2$ is H or M, $R_6$ is not $CH_3$;

$(CH_2)_nCHNH_2CO_2H$, wherein n=1–8;

$CH(CO_2H)NHCONH_2$; or, $C_5H_4N$; and wherein $R_2$ is selected from H, $CH_3$, $(CH_2)_nCH_3$ wherein n=1–8, $(CH_2)_xO(CH_2)_yCH_3$ or $(CH_2)_xCO(CH_2)_yCH_3$ wherein x+y=2–7, or M, wherein M is a metal counterion or a low molecular weight organic cation.

3. The method of claim 2 wherein the transient expression enhancing agent comprises an amino acid derivative selected from the group consisting of 3-methyl-L-histidine, α-ketoglutaric acid, β-alanine, carnosine, citrulline, creatine, folic acid, glutathione, hippuric acid, homoserine, N-(4-aminobenzyl)-L-glutamic diethylester, N-carbamyl aspartic acid, N-formyl-L-methionine, and ornithine.

4. The method of claim 2, wherein $R_1$ is non-polar or hydrophobic at a pH between 4.5 and 10.5.

5. The method of claim 1, wherein the transient expression enhancing agent comprises a sulfionic acid derivative having the formula:

$$R_7—SO_2—OR_8$$

wherein $R_7$ is a lower alkyl, aryl, substituted lower alkyl, aryl, substituted lower alkyl, or substituted aryl; and $R_8$ is a hydrogen, a metal counterion, or a low molecular weight organic cation.

6. The method of claim 5 wherein $R_7$ is an amino substituted lower alkyl group or an amino substituted aryl group.

7. The method of claim 5 wherein the sulfonic acid derivative is selected from the group consisting of 3-aminobenzene sulfonic acid, taurine, and salts thereof.

8. The method of claim 1, wherein the transient expression enhancing agent comprises a glycosaminoglycan.

9. The method of claim 8, wherein the glycosaminoglycan is a sulfonated amino polysaccharide.

10. The method of claim 9, wherein the sulfonated amino polysaccharide comprises an N-acetylated amino polysaccharide.

11. The method of claim 10, wherein the N-acetylated amino polysaccharide is chondroitin sulfate.

12. The method of claim 1 wherein the transient expression enhancing agent comprises a compound selected from the group consisting of adrenaline, coenzyme B12, and methylcobalamin.

13. The method of claim 1, wherein the agent comprises: benzoic acid and 4-ethylbenzoic acid; or benzoate buffer and chondroitin sulfate; or benzoate buffer and glutamic acid; or glutathione, methionine, glycine, α-amino-n-butyric acid, taurine, phenylalanine, benzoate buffer, and alanine; or 4-ethylbenzoic acid, benzoic acid, and chondroitin sulfate; or α-lipoic acid and chondroitin sulfate.

14. The method of claim 1, wherein the concentration of the transient expression enhancing agent is 1–15 mM.

15. The method of claim 9, wherein the concentration of the transient expression enhancing agent is 0.01–0.5 mM.

16. The method of claim 11, wherein the chondroitin sulfate has an average molecular mass of no greater than 9000 daltons.

17. The method of claim 11, wherein the chondroitin sulfate has an average molecular mass of no greater than 4000 daltons.

18. The method of claim 1, wherein the cell is contacted with a first transient expression enhancing agent prior to and during the introduction into the cell of the foreign DNA, wherein the agent comprises at least one compound having the formula:

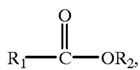

wherein $R_1$ is:

$CHNH_2R_3$, wherein $R_3$ is the side chain of a naturally occurring amino acid;

$C_6H_4R_4$, wherein $R_4$ is H, $CH_3$, $(CH_2)_nCH_3$, $NH_2$, $COCH_3$, $CO(CH_2)_nCH_3$, $C(CH_3)_3$, $CH(CH_3)_2$, $(CH_2)_nCH(CH_3)_2$, $(CH_2)_nCOCH_3$, $OCH_3$, or $O(CH_2)_nCH_3$, wherein n=1–3;

$CHNH_2(CH_2)_nR_5$, wherein n=1–7 and $R_5$ is $CH_3$, OH, $CONH_2$, $C_6H_4OH$, or $CONHNH_2$;

$(CH_2)_nR_6$, wherein n=1–9 and $R_6$ is an indole group, $NCH_3C(=NH)NH_2$, $SCH_3$, $NH_2$, $CH_3$, $CO_2H$, $CONH_2$, or $NHC(=NH)NH_2$, provided that when n=2 and $R_2$ is H or M, $R_6$ is not $CH_3$;

$(CH_2)_nCHNH_2CO_2H$, wherein n=1–8;

$CH(CO_2H)NHCONH_2$; or, $C_5H_4N$; and wherein $R_2$ is H, $CH_3$, $(CH_2)_nCH_3$ wherein n=1–8, $(CH_2)_xO(CH_2)_yCH_3$ or $(CH_2)_xCO(CH_2)_yCH_3$ wherein x+y=2–7, or M, wherein M is a metal counterion or a low molecular weight organic cation;

or the first transient expression enhancing agent comprises a compound having the formula:

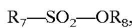

wherein $R_7$ is a lower alkyl, aryl, substituted lower alkyl, or substituted aryl; and $R_8$ is a hydrogen, a metal counterion, or a low molecular weight organic cation;

and following the introduction of the foreign DNA, the cell is contacted with a second transient expression enhancing agent, wherein the second agent comprises a sulfonated amino polysaccharide.

19. The method of claim 18, wherein the cell further is continuously exposed to the first agent after the introduction of the foreign DNA into the cell.

20. The method of claim 1, wherein the cell is selected from the group consisting of a stably transformed cell, a tumor cell line, a hybridoma cell, and a primary cultured cell.

21. The method of claim 20, wherein the cell is a SW480 P3 cell.

22. The method of claim 1, wherein the protein encoded by the foreign gene is harvested.

23. The method of claim 1, wherein the foreign DNA is introduced into the cell by a method selected from the group consisting of lipofection, a viral vector, exposure of cells to coprecipates of calcium phosphate, and transfection in the presence of a dendrimer.

24. The method of claim 23, wherein the DNA is introduced into the cell by a viral vector, and the viral vector comprises an adenovirus.

25. The method of claim 1, wherein the agent contains at least one acidic moiety and at least one moiety that is hydrophobic at a pH between 4.5 and 10.5, and wherein the acidic group may be modified to form a salt or an ester.

26. The method of claim 25, wherein the acidic moiety is hydrophobic and organic at a pH between 4.5 and 10.5.

27. The method of claim 1 wherein foreign protein is detected in the cell after maintaining the cell for at least eight days in the non-selective medium.

28. The method of claim 1 wherein foreign protein is detected in the cell after maintaining the cell for at least fourteen days in the non-selective medium.

29. The method of claim 1 wherein foreign protein is detected in the cell after maintaining the cell for at least twenty days in the non-selective medium.

30. The method of claim 1 wherein foreign protein is detected in the cell after maintaining the cell for at least 25 days in the non-selective medium.

31. A method of enhancing the transient expression of a foreign gene in a eukaryotic cell in vitro comprising:

introducing into the cell a molecule of foreign DNA that encodes a protein in a form capable of being expressed in the cell;

contacting the cell with a first agent during the introduction into the cell of the foreign DNA, wherein the agent comprises at least one compound having the formula:

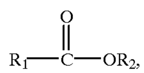

wherein $R_1$ is:

$CHNH_2R_3$, wherein $R_3$ is the side chain of a naturally occurring amino acid;

$C_6H_4R_4$, wherein $R_4$ is H, $CH_3$, $(CH_2)_nCH_3$, $NH_2$, $COCH_3$, $CO(CH_2)_nCH_3$, $C(CH_3)_3$, $CH(CH_3)_2$, $(CH_2)_nCH(CH_3)_2$, $(CH_2)_nCOCH_3$, $OCH_3$, or $O(CH_2)_nCH_3$, wherein n=1–3;

$CHNH_2(CH_2)_nR_5$, wherein n=1–7 and $R_5$ is $CH_3$, OH, $CONH_2$, $C_6H_4OH$, or $CONHNH_2$;

$(CH_2)_nR_6$, wherein n=1–9 and $R_6$ is an indole group, $NCH_3C(=NH)NH_2$, $SCH_3$, $NH_2$, $CH_3$, $CO_2H$, $CONH_2$, or $NHC(=NH)NH_2$, provided that when n=2 and $R_2$ is H or M, $R_6$ is not $CH_3$;

$(CH_2)_nCHNH_2CO_2H$, wherein n=1–8;

$CH(CO_2H)NHCONH_2$; or, $C_5H_4N$; and wherein $R_2$ is H, $CH_3$, $(CH_2)_nCH_3$ wherein n=1–8, $(CH_2)_xO(CH_2)_yCH_3$ or $(CH_2)_xCO(CH_2)_yCH_3$ wherein x+y=2–7, or M, wherein M is a metal counterion or a low molecular weight organic cation;

or the first agent comprises at least one chemical compound having the formula:

$R_7$—$SO_2$—$OR_8$, wherein $R_7$ is a lower alkyl, aryl, substituted lower alkyl, or substituted aryl; and $R_8$ is a hydrogen atom, a metal counterion, or a low molecular weight organic cation;

and during and/or following the introduction of the foreign DNA, the cell is contacted with a second agent, wherein the second agent comprises at least one sulfonated amino polysaccharide or wherein the second agent comprises at least one chemical compound having the formula:

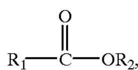

wherein $R_1$ is:

$CHNH_2R_3$, wherein $R_3$ is the side chain of a naturally occurring amino acid;

$C_6H_4R_4$, wherein $R_4$ is H, $CH_3$, $(CH_2)_nCH_3$, $NH_2$, $COCH_3$, $CO(CH_2)_nCH_3$, $C(CH_3)_3$, $CH(CH_3)_2$, $(CH_2)_nCH(CH_3)_2$, $(CH_2)_nCOCH_3$, $OCH_3$, or $O(CH_2)_nCH_3$, wherein n=1–3;

$CHNH_2(CH_2)_nR_5$, wherein n=1–7 and $R_5$ is $CH_3$, OH, $CONH_2$, $C_6H_4OH$, or $CONHNH_2$;

$(CH_2)_nR_6$, wherein n=1–9 and $R_6$ is an indole group, $NCH_3C(=NH)NH_2$, $SCH_3$, $NH_2$, $CH_3$, $CO_2H$, $CONH_2$, or $NHC(=NH)NH_2$, provided that when n=2 and $R_2$ is H or M, $R_6$ is not $CH_3$;

$(CH_2)_nCHNH_2CO_2H$, wherein n=1–8;

$CH(CO_2H)NHCONH_2$; or, $C_5H_4N$; and wherein $R_2$ is H, $CH_3$, $(CH_2)_nCH_3$ wherein n=1–8, $(CH_2)_xO(CH_2)_yCH_3$ or $(CH_2)_xCO(CH_2)_yCH_3$ wherein x+y=2–7, or M, wherein M is a metal counterion or a low molecular weight organic cation;

or the second agent comprises at least one chemical compound having the formula:

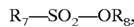

wherein $R_7$ is a lower alkyl, aryl, substituted lower alkyl, or substituted aryl; and $R_8$ is a hydrogen, a metal counterion, or a low molecular weight organic cation; and wherein the first agent is one that has a value for X that is greater than 25 when X is calculated according to the formula:

$$X = 100 - \frac{(A \times 100)}{C}$$

and wherein the second agent is one that has a value of $G_7$ or $G_{14}$ that is greater than 25, wherein $G_7$ or $G_{14}$ is calculated according to the formula:

$$G_7 \text{ or } G_{14} = 100 - \frac{(A \times 100)}{C}$$

wherein for both X or $G_7$ or $G_{14}$, "A" is the amount of the protein encoded by the foreign gene expressed in a first cell that is contacted with the first and the second agent, and "C" is the amount of protein expressed in a second cell that is not contacted with the first or the second agent.

32. The method of claim 31, wherein the cell is contacted with the first agent prior to, continuously after, or both prior to and continuously after the introduction of the foreign DNA.

33. The method of claim 31, wherein the first agent comprises benzoate buffer, and the second agent comprises chondroitin sulfate.

34. The method of claim 31, wherein the first agent comprises benzoic acid and 4-ethylbenzoic acid, and the second agent comprises benzoate buffer and chondroitin sulfate.

35. The method of claim 31, wherein the first agent comprises benzoate buffer and glutamic acid, and the second agent comprises chondroitin sulfate.

36. The method of claim 31, wherein the cell is contacted with the first agent for about 24 hours prior to the introduction into the cell of the foreign DNA.

37. A method of enhancing the transient expression of a foreign gene in a eukaryotic cell in vitro comprising:

introducing into the cell a molecule of foreign DNA that encodes a protein in a form capable of being expressed in the cell; and, contacting the cell before, during, or after introducing the DNA with a transient expression enhancing agent;

wherein the transient expression enhancing agent comprises:

a compound selected from the group consisting of 3-methyl-L-histidine, α-ketoglutaric acid, 9-alanine, carnosine, citrulline, creatine, glutathione, hippuric acid, homoserine, N-carbamyl aspartic acid, N-formyl-L-methionine, ornithine, N-(4-aminobenzyl)-L-glutamic diethylester, ethyl-4-acetylbutyrate, adrenaline, methylcobalamin, benzoic acid, benzoate buffer, 4-ethylbenzoic acid and a sulfonated N-acetylated amino polysaccharide, disaccharide monomeric units derived from Type C chondroitin sulfate, polymannose, mannose; or a sulfonic acid derivative having the formula:

$$R_7—SO_2—OR_8$$

wherein $R_7$ is a lower alkyl, aryl, substituted lower alkyl, aryl, substituted lower alkyl, or substituted aryl, and $R_8$ is a hydrogen, a metal counterion, or a low molecular weight organic cation; or benzoic acid and 4-ethylbenzoic acid; or benzoic acid and 4-ethylbenzoic acid and chondroitin sulfate; or benzoic acid and L-glutamine; or benzoate buffer and chondroitin sulfate; or benzoate buffer and glutamic acid; or lipoic acid and chondroitin sulfate; or benzoate buffer, chondroitin sulfate, and L-glutamine; or chondroitin sulfate and L-glutamine; or butyrate buffer and L-glutamine; or a mixture comprising glutathione, methionine, glycine, α-amino-n-butyric acid, taurine, phenylalanine, benzoate buffer, and alanine.

* * * * *

UNITED STATES PATENT AND TRADEMARK OFFICE
CERTIFICATE OF CORRECTION

PATENT NO. : 6,146,847
DATED : November 14, 2000
INVENTOR(S) : R.A. Goffe et al.

It is certified that error appears in the above-identified patent and that said Letters Patent is hereby corrected as shown below:

Column 43,
Line 30, (Claim 1, line 13), "five days to" should read -- five days in --

Column 44,
Line 20, (Claim 5, line 2), "sulfionic" should read -- sulfonic --

Column 45,
Line 57, (Claim 23, line 4), "coprecipates" should read -- coprecipitates --

Column 46,
Line 20, (Claim 31, line 7), after "wherein the" insert -- first --
Line 21, (Claim 31, line 8), after "at least one" insert -- chemical --
Line 58, (Claim 31, line 34), "or substituted aryl" should read -- or substituted lower aryl --

Column 47,
Line 34, (Claim 31, line 68), "or substituted aryl" should read -- or substituted lower aryl --

Column 48,
Line 26, (Claim 37, line 11), "9-alanine" should read -- β-alanine --

Signed and Sealed this

Twenty-third Day of October, 2001

*Attest:*

NICHOLAS P. GODICI

*Attesting Officer*

*Acting Director of the United States Patent and Trademark Office*